US008338385B2

(12) United States Patent
Kim et al.

(10) Patent No.: US 8,338,385 B2
(45) Date of Patent: *Dec. 25, 2012

(54) HYBRID HEPATOCYTE GROWTH FACTOR GENE HAVING HIGH EXPRESSION EFFICIENCY OF TWO HETEROTYPES OF HEPATOCYTE GROWTH FACTOR

(75) Inventors: Jong-Mook Kim, Seoul (KR); Woong Hahn, Gyeonggi-do (KR)

(73) Assignee: ViroMed Co., Ltd. (KR)

( * ) Notice: Subject to any disclaimer, the term of this patent is extended or adjusted under 35 U.S.C. 154(b) by 4 days.

This patent is subject to a terminal disclaimer.

(21) Appl. No.: 12/908,765

(22) Filed: Oct. 20, 2010

(65) Prior Publication Data

US 2012/0010273 A1 Jan. 12, 2012

Related U.S. Application Data

(60) Continuation of application No. 11/957,170, filed on Dec. 14, 2007, now Pat. No. 7,838,505, which is a division of application No. 10/944,277, filed on Sep. 20, 2004, now Pat. No. 7,812,146, which is a continuation of application No. PCT/KR03/00548, filed on Mar. 20, 2003.

(30) Foreign Application Priority Data

Mar. 20, 2002 (KR) .................. 10-2002-0015074

(51) Int. Cl.
*A01N 43/04* (2006.01)
*C12N 15/63* (2006.01)
*C12N 15/85* (2006.01)
*C12N 15/86* (2006.01)
*C12N 1/20* (2006.01)
*C12N 1/19* (2006.01)
*C12N 15/00* (2006.01)
*A61K 48/00* (2006.01)
*A61K 31/70* (2006.01)
*C12P 21/00* (2006.01)

(52) U.S. Cl. ................ 514/44 R; 435/320.1; 435/325; 435/252.3; 435/252.33; 435/254.2; 435/69.1; 435/69.4; 435/70.1; 435/71.1; 536/23.51

(58) Field of Classification Search ............... 514/44 R
See application file for complete search history.

(56) References Cited

U.S. PATENT DOCUMENTS

| | | | |
|---|---|---|---|
| 5,328,836 A | 7/1994 | Shima et al. | |
| 5,500,354 A | 3/1996 | Kitamura et al. | |
| 5,580,859 A | 12/1996 | Felgner et al. | |
| 5,587,359 A | 12/1996 | Higashio et al. | |
| 5,652,225 A | 7/1997 | Isner | |
| 5,693,622 A | 12/1997 | Wolff et al. | |
| 6,013,624 A | 1/2000 | Goldberg et al. | |
| 6,121,246 A | 9/2000 | Isner | |
| 6,248,722 B1 | 6/2001 | Morishita et al. | |
| 6,258,787 B1 | 7/2001 | Isner | |
| 6,316,419 B1 | 11/2001 | Leiden et al. | |
| 6,413,942 B1 | 7/2002 | Felgner et al. | |
| 6,498,144 B1 | 12/2002 | Goldberg et al. | |
| 6,706,694 B1 | 3/2004 | Wolff et al. | |
| 6,887,477 B1 | 5/2005 | Nagano et al. | |
| 7,285,540 B2 | 10/2007 | Morishita et al. | |
| 7,745,174 B2 | 6/2010 | Kim et al. | |
| 7,812,146 B2 | 10/2010 | Kim et al. | |
| 7,838,505 B2 | 11/2010 | Kim et al. | |
| 2002/0172663 A1 | 11/2002 | Palasis | |
| 2003/0148968 A1 | 8/2003 | Hammond et al. | |
| 2003/0171287 A1 | 9/2003 | Morishita et al. | |
| 2004/0105882 A1 | 6/2004 | Morishita et al. | |
| 2004/0228834 A1 | 11/2004 | Isner et al. | |
| 2006/0286072 A1 | 12/2006 | Giordano et al. | |
| 2007/0059288 A1 | 3/2007 | Dinsmore et al. | |
| 2008/0268030 A1 | 10/2008 | Morishita et al. | |
| 2009/0004260 A1 | 1/2009 | Morishita et al. | |
| 2009/0082293 A1 | 3/2009 | Giordano et al. | |
| 2009/0202606 A1 | 8/2009 | Kim et al. | |
| 2009/0258932 A1 | 10/2009 | Kim et al. | |

FOREIGN PATENT DOCUMENTS

| | | |
|---|---|---|
| JP | 11-246433 | 9/1999 |
| WO | WO 98/50079 A2 | 11/1998 |
| WO | WO 99/45775 A1 | 9/1999 |
| WO | WO 01/34208 A1 | 5/2001 |
| WO | WO 02/089856 A1 | 11/2002 |

OTHER PUBLICATIONS

Deng, et al., "Secretory Expression of the Deleted Variant of Human Hepatocyte Growth Factor (hdHGF) in *Pichia pastoris*," Chinese Journal of Biochemistry and Molecular Biology, 2001, 17:590-594, China Academic Journal Electronic Publishing House, Beijing, China. English Abstract is on face page of document.

Espacenet Database, English language abstract of JP 11-246433 A, published Sep. 14, 1999 (listed as document FP2 on the accompanying form PTO/SB/08A).

European Search Report for European Application No. EP 0 3 744 561, mailed Apr. 18, 2006, European Patent Office, Munich, Germany.

Gardilik, et al., "Vectors and delivery systems in gene therapy," Med Sci Monit 11(4):RA110-121 (2005).

Kato et al., "Nonviral HVJ (hemagglutinating virus of Japan) liposome-mediated retrograde gene transfer of human hepatocyte growth factor into rat nervous system promotes functional and histological recovery of the crushed nerve," Neuroscience Research, 52, pp. 299-310, Elsevier Ireland Ltd and the Japan Neuroscience Society (2005).

(Continued)

*Primary Examiner* — Valarie Bertoglio
(74) *Attorney, Agent, or Firm* — Sterne, Kessler, Goldstein & Fox P.L.L.C.

(57) ABSTRACT

The present invention relates to a hybrid Hepatocyte Growth Factor (HGF) gene which is prepared by inserting an inherent or foreign intron between exons 4 and 5 in HGF cDNA, which has a base sequence of SEQ ID NO: 2. The gene has high expression efficiency and simultaneously expresses two heterotypes of HGF and dHGF (deleted variant HGF). Further the gene may be used for treating or preventing ischemic or liver diseases.

16 Claims, 12 Drawing Sheets

OTHER PUBLICATIONS

Kisselev, L., "Polypeptide Release Factors in Prokaryotes and Eukaryotes: Same Function, Different Structure," Structure, 2002, 10, pp. 8-9, Elsevier Science Ltd., Cambridge, Massachusetts, USA.

Liu et al., "Development of non-viral vectors for systemic gene delivery," Journal of Controlled Release 78:1-3:259-266, Elsevier Science B.V. (Jan. 2002).

Liu, Y., "The human hepatocyte growth factor receptor gene: complete structural organization and promoter characterization," Gene 215: 159-169, Elsevier/North Holland (1998).

Miyazawa, K., et al., "Molecular Cloning and Sequence Analysis of eDNA for Human Hepatocyte Growth Factor," Biochem. Biophys. Res. Commun. 163:967-973, Academic Press (1989).

Nakamura, T., et al., "Molecular cloning and expression of human hepatocyte growth factor," Nature 342:440-443, Nature Publishing Group (1989).

NCBI Entrez, GenBank Database, Accession No. AC004960, "*Homo sapiens* PAC clone RP5-1098B1 from 7q11.23-q21, complete sequence," 51 pages (first available 1998).

Ngo et al., in The Protein Folding Problem and Tertiary Structure Prediction, 1994, Merz et al. (ed.), Birkhauser, Boston, MA, pp. 433 and 492-495.

Patil, et al., "DNA-based Therapeutics and DNA Delivery Systems: A Comprehensive Review," The AAPS Journal 9(1) Article 9:E61-E77 (2005).

Potrykus. Gene transfer to cereals: an assessment, Biotechnology, 1990, 8(6):535-542.

Romano et al., "Gene Transfer Technology in Therapy: Current Applications and Future Goals," Stem Cells 17:191-202, AlphaMed Press (1999).

Rubin, et al., "A broad-spectrum human lung fibroblast-derived mitogen is a variant of hepatocyte growth factor," Proc. Nat/. Acad. Sci. USA, 1991, 88:415-419, Proceedings of the National Academy of Sciences of the United States of America, 500 5th St., Washinton, DC 20001.

Schmitz et al., "Gene therapy for liver diseases: recent strategies for treatment of viral hepatitis and liver malignancies," Gut 50:1:130-135 (Jan. 2002).

Seki, T., et al., "Isolation and Expression of eDNA for Different Forms of Hepatocyte Growth Factor from Human Leukocyte," Biochem. Biophys. Res. Commun. 172:321-327, Academic Press (1990).

Seki, T., et al., "Organization of the human hepatocyte growth factor-encoding gene," Gene 102:213-219, Elsevier/North-Holland (1991).

Shima, N., et al., "Hepatocyte Growth Factor and its Variant with a Deletion of Five Amino Acids are Distinguishable in their Biological Activity and Tertiary Structure," Biochem. Biophys. Res. Commun. 200:808-815, Academic Press (1994).

Thomas, et al., "Progress and Problems with the use of viral vectors for gene therapy," Nature Reviews Genetics 4:346-358, Nature Publishing Group (2003).

Warnecke C. et al., "Efficient transcription of the human angiotensin II type 2 receptor gene requires intronic elements," Biochemical journal, 1999, 340 (1), pp. 17-24, Portland Press, Colchester, Great Britain.

Wishart et al., "A Single Mutation Converts a Novel Phosphotyrosine Binding into a Dual-Specificity Phosphatase," Journal of Biological Chemistry, 1995, 270 (45), pp. 26782-26785, American Society for Biochemistry and Molecular Biology, Bethesda, MD, USA.

Witkowski et al., "Conversion of a A-Ketoacyl Synthase to a Malonyl Decarboxylase by Replacement of the Active-Site Cysteine with Glutamine," Biochemistry, 1999, 38:36, pp. 11643-11650, American Chemical Society, Washington, DC, USA.

Yang, et al., "Sustained Expression of Naked Plasmid DNA Encoding Hepatocyte Growth Factor in Mice Promotes Liver and Overall Body Growth," Hepatology 33:848-859, American Assoc. for the Study of Liver Disease (2001).

Office Action for U.S. Appl. No. 10/944,277 (now U.S. Pat. No. 7,812,146), mailed Jan. 9, 2008.

Office Action for U.S. Appl. No. 10/944,277 (now U.S. Pat. No. 7,812,146), mailed Feb. 13, 2009.

Notice of Allowance for U.S. Appl. No. 10/944,277 (now U.S. Pat. No. 7,812,146), mailed May 29, 2009.

Notice of Allowance for U.S. Appl. No. 10/944,277 (now U.S. Pat. No. 7,812,146), mailed Oct. 23, 2009.

Notice of Allowance for U.S. Appl. No. 12/650,860 (now U.S. Pat. No. 7,745,174), mailed Mar. 10, 2010.

Office Action for U.S. Appl. No. 11/957,170 (now U.S. Pat. No. 7,838,505), mailed Jan. 28, 2010.

Notice of Allowance for U.S. Appl. No. 11/957,170 (now U.S. Pat. No. 7,838,505), mailed Jul. 19, 2010.

Office Action for Co-pending U.S. Appl. No. 12/359,137, mailed Apr. 28, 2011.

Office Action for Co-pending U.S. Appl. No. 12/421,425, mailed Aug. 19, 2010.

Office Action for Co-pending U.S. Appl. No. 12/421,425, mailed Dec. 17, 2010.

U.S. Appl. No. 13/045,460, filed Mar. 10, 2011 (not yet published).

HepG2 genomic DNA

PCR

① Primers SEQ ID No.3 + SEQ ID.No.4 → F2
② Primers SEQ ID No.3 + SEQ ID No.5 → F3
③ Primers SEQ ID No.6 + SEQ ID No.7 → F5
④ Primers SEQ ID No.8 + SEQ ID No.7 → F7
⑤ Primers SEQ ID No.9 + SEQ ID No.7 → F8
⑥ Primers SEQ ID No.10 + SEQ ID No.7 → F6

Inserting into pGEM-T-easy

HGF-Fs pGEM-T-easy-HGF-F2
pGEM-T-easy-HGF-F3
pGEM-T-easy-HGF-F5
pGEM-T-easy-HGF-F7
pGEM-T-easy-HGF-F8
pGEM-T-easy-HGF-F6

HYBRID HEPATOCYTE GROWTH FACTOR GENE HAVING HIGH EXPRESSION EFFICIENCY OF TWO HETEROTYPES OF HEPATOCYTE GROWTH FACTOR

CROSS-REFERENCE TO RELATED APPLICATIONS

This application is a continuation of U.S. application Ser. No. 11/957,170, filed Dec. 14, 2007, now U.S. Pat. No. 7,838,505, which is a divisional of U.S. application Ser. No. 10/944,277, filed Sep. 20, 2004, now issued U.S. Pat. No. 7,812,146, which is a continuation of International Application No. PCT/KR03/00548, filed Mar. 20, 2003, both each of which are is herein incorporated by reference.

REFERENCE TO SEQUENCE LISTING SUBMITTED ELECTRONICALLY VIA EFS-WEB

The content of the electronically submitted sequence listing (Name: sequence listing.ascii.txt, Size: 29,896 bytes; Date of Creation: Oct. 12, 2010) filed with the application is incorporated herein by reference in its entirety.

BACKGROUND OF THE INVENTION

1. Field of the Invention

The present invention relates to a highly efficient hybrid Hepatocyte Growth Factor (HGF) gene which simultaneously expresses two heterotypes of HGF.

2. Related Art

The present invention relates to a hybrid HGF gene prepared by inserting an inherent or foreign intron between exons 4 and 5 in HGF cDNA, which has higher expression efficiency than HGF cDNA and simultaneously expresses two heterotypes of HGF and dHGF (deleted variant HGF).

HGF is a heparin binding glycoprotein called a scatter factor. A gene encoding HGF is located at chromosome 7q21.1 and comprises 18 exons and 17 introns, having the nucleotide sequence of SEQ ID NO: 1 (Seki T., et al., *Gene* 102:213-219 (1991)). A transcript of about 6 kb is transcribed from the HGF gene, and then, a polypeptide HGF precursor consisting of 728 amino acids is synthesized therefrom. Simultaneously, a polypeptide of dHGF precursor consisting of 723 amino acids is also synthesized by an alternative splicing of the HGF gene. The biologically inactive precursors may be converted into active forms of disulfide-linked heterodimer by protease in serum. In the heterodimers, the alpha chain having a high molecular weight forms four kringle domains and an N-terminal hairpin loop like a preactivated peptide region of plasminogen. The kringle domains of a triple disulfide-bonded loop structure consisting of about 80 amino acids may play an important role in protein-protein interaction. The low molecular weight beta chain forms an inactive serine protease-like domain. dHGF consisting 723 amino acids is a polypeptide with deletion of five amino acids in the 1st kringle domain of the alpha chain, i.e., F, L, P, S and S.

It has been recently reported that both of HGF and dHGF have several biological functions, e.g., promoting the growth and morphogenesis of epithelial cell, melanocyte and endothelial cell. However, they are different in terms of immunological or biological properties.

For example, HGF shows about 20-fold, 10-fold and 2-fold higher activities than dHGF in promoting DNA synthesis in human umbilical cord venous endothelial cell, arterial smooth muscle cell and NSF-60 (murine myeloblast cell), respectively. dHGF shows about 3-fold and 2-fold higher activities than HGF in promoting DNA synthesis of LLC-PK1 (pig kidney epithelial cell), and OK (American opossum kidney epithelial cell) and mouse interstitial cell, respectively. HGF has a 70-fold higher solubility in PBS than dHGF. Several anti-dHGF monoclonal antibodies recognize only dHGF, but not HGF or a reduced form of dHGF, which implies structures of HGF and dHGF are different. Accordingly, the simultaneous synthesis of HGF and dHGF in vivo suggests that they biologically interact with each other (Shima, N. et al., *Biochemical and Biophysical Research Communications* 200:808-815 (1994)).

HGF secreted from mesoderm-derived cells has various biological functions, e.g., 1) inducing epithelial cells into a tubular structure; 2) stimulating vascularization from endothelial cells in vitro and in vivo; 3) regeneration of liver and kidney, owing to its anti-apoptosis activity; 4) organogenesis of kidney, ovary and testis; 5) controlling osteogenesis; 6) stimulating the growth and differentiation of erythroid hematopoietic precursor cells; and 7) axon sprouting of neurons (Stella, M. C. and Comoglio, P. M., *The International Journal of Biochemistry & Cell Biology* 31:1357-1362 (1999)). Based on these various functions, HGF or a gene encoding HGF may be developed as a therapeutic agent for treating ischemic or liver diseases. Actually, in vivo, the HGF may exist as either HGF or dHGF, and therefore, the coexpression of HGF and dHGF is important for maximizing the therapeutic effect. Accordingly, the present inventors have endeavored to develop a hybrid HGF gene which can simultaneously express HGF and dHGF with a high efficiency for gene therapy.

SUMMARY OF THE INVENTION

Accordingly, it is a primary object of the present invention to provide a hybrid HGF gene which simultaneously expresses two heterotypes of HGF.

In accordance with one aspect of the present invention, there is provide the hybrid HGF gene having an inherent or foreign intron is inserted between exons 4 and 5 of HGF cDNA.

It is another object of the present invention to provide a recombinant vector comprising the hybrid HGF gene and a microorganism transformed with the above vector.

It is a still further object of the present invention to provide a pharmaceutical composition for treating or preventing ischemic or liver diseases, which comprises the HGF gene.

BRIEF DESCRIPTION OF THE DRAWINGS

The above and other objects and features of the present invention will become apparent from the following description of the invention, when taken in conjunction with the accompanying drawings which respectively show.

DETAILED DESCRIPTION OF THE INVENTION

Figure 1:
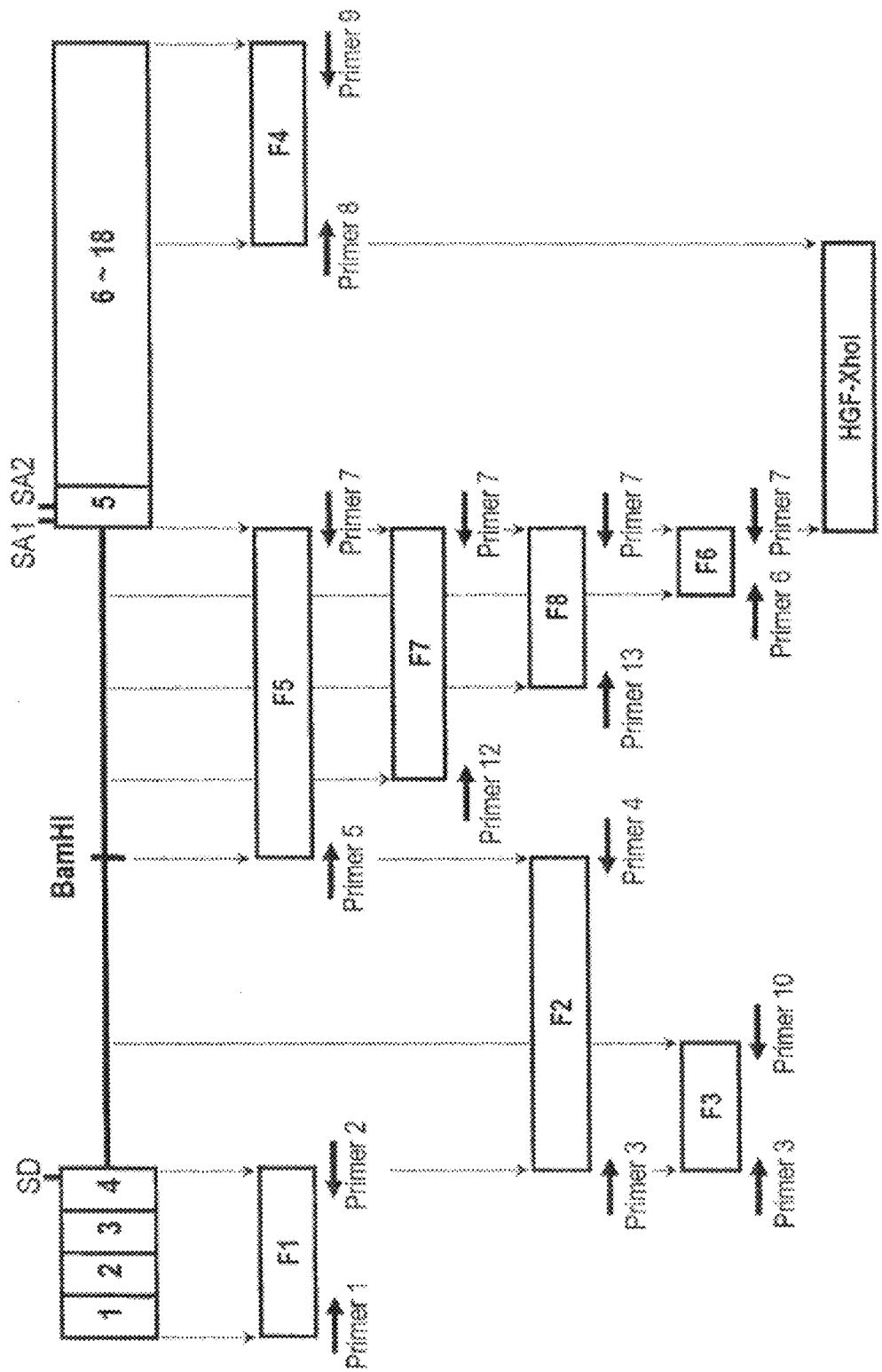
FIG. 1: a schematic diagram of HGF-X prototype illustrating the positions of the gene fragments.

The hybrid Hepatocyte Growth Factor (HGF) gene of the present invention comprises cDNA corresponding to the exons 1 to 18, and an inherent or foreign intron inserted between exons 4 and 5 of the cDNA. The intron comprises a fragment of the inherent intro or a recombinant sequence.

An embodiment of the hybrid HGF gene of the present invention comprising the inherent intron is 7113 bp long and has the nucleotide sequence of SEQ ID NO: 2. The hybrid HGF gene simultaneously expresses both HGF and dHGF, and has higher expression efficiency than HGF cDNA.

Codon degeneracy enables the hybrid HGF gene of the present invention to be modified or changed in the coding and/or non-coding region without altering the amino acid sequence of the protein and the expression of the gene. Accordingly, polynucleotides which is substantially identical to the hybrid HGF gene of SEQ ID NO:2, and the fragments thereof fall within the scope of the invention. "Substantially identical" means that the sequence homology is not less than 80%, preferably not less than 90%, and more preferably not less than 95%.

A hybrid HGF gene may comprise a fragment of inherent intron optionally having a small recombinant sequence inserted thereinto between exons 4 and 5 of HGF cDNA. Herein, such a hybrid HGF gene comprising a fragment of inherent intron designates "HGF-X". HGFX-6, HGF-X7 and HGF-X8 having the nucleotide sequence of SEQ ID Nos: 19 to 21, respectively, are preferred.

The hybrid HGF gene of the present invention is synthesized and inserted into an expression vector, according to the known genetic engineering methods. Then, the vector can be introduced into an appropriate host cells such as *E. coli* and yeast. For example, *Escherichia coli* Top10F' may be transfected with HGF-X7 gene of the present invention. *Escherichia coli* Top10F' pCK-HGFX7 and *Escherichia coli* Top10F' pCP-HGFX7 then obtained were deposited as the accession numbers KCCM-10361 and KCCM-10362, respectively, on Mar. 12, 2002.

By using the transformed cells, the gene of the present invention and the protein encoded thereby may be produced on a large scale.

The vector of the present invention may selectively comprise sequence(s) for regulating gene expression such as promoter or terminator, self-replication sequence and secretory signal, depending on host cells.

Further, the present invention comprises a pharmaceutical composition for treating or preventing ischemic and liver diseases, which comprises the hybrid HGF gene or the vector comprising the gene as an active ingredient. Preferably, the composition is formulated for injection.

The composition of the present invention may further comprise pharmaceutically acceptable carriers. Any of the conventional procedures in the pharmaceutical field may be used to prepare oral formulations such as tablets, capsules, pills, granules, suspensions and solutions; rejection formulations such as solutions, suspensions, or dried powders that may be mixed with distilled water before injection; locally-applicable formulations such as ointments, creams and lotions; and other formulations.

Carriers generally used in the pharmaceutical field may be employed in the composition of the present invention. For example, orally-administered formulations may include binders, emulsifiers, disintegrating agents, excipients, solubilizing agents, dispersing agents, stabilizing agents, suspending agents, coloring agents or spicery. Injection formulations may comprise preservatives, unagonizing agents, solubilizing agents or stabilizing agents. Preparation for local administration may contain bases, excipients, lubricants or preservatives. Any of the suitable formulations known in the art (Remington's Pharmaceutical Science [the new edition], Mack Publishing Company, Eaton Pa.) may be used in the present invention.

The inventive composition can be clinically administered as various oral and parenteral formulations. A suitable formulation may be prepared using such excipients as additives, enhancers, binders, wetting agents, disintegrating agents and surfactants, or diluents. Solid formulations for oral administration include pills, tablets, dusting powder, granules and capsules. Those solid formulations may be prepared by mixing one or more excipients, e.g. starch, calcium carbonate, sucrose, lactose and gelatin with dibenzylbuthyllacton lignan derivatives. Also, lubricants such as magnesium stearate and talc may be included in the present formulation. Liquid formulations for oral administration include suspension, solution, emulsion and syrup. Those formulations may contain wetting agents, sweeteners, aromatics and preservatives, in addition to general simple diluents such as water and liquid paraffin. Formulations for parenteral administration include sterilized aqueous solution, suspension, emulsion, freeze-dried alternative treatment and suppositories. Water-insoluble excipients and suspending agents comprise vegetable fats such as propylene glycol, polyethylene glycol and olive oil, and injectable esters such as ethyl oleate. Witepsol®, Macrogol®, Tween® 61, cacao fats, laurin fats and glycerogelatins may be used as bases of suppositories.

The inventive composition may be administered orally or via parenteral routes such as intravenous, intramuscular, subcutaneous, intraabdominal, sternal and arterial injection or infusion, or topically through rectal, intranasal, inhalational or intraocular administration.

It should be understood that the typical daily dose of composition of the present invention ought to be determined in light of various relevant factors including the conditions to be treated, the chosen route of administration, the age, sex and body weight of the individual patient, and the severity of the patient's symptom, and can be administrated in a single dose or in divided dose. Therefore, the daily dose should not be construed as a limitation to the scope of the invention in any way.

The following Examples are given for the purpose of illustration only, and are not intended to limit the scope of the invention.

EXAMPLE 1

Preparation of Hybrid Gene Constructs Encoding Human HGF (1) Cloning of HGF Gene Fragments Obtained from Genomic DNA Human HepG2 cells (ATCC Accession NO: HB-8065) were suspended in TES buffer (10 mM Tris-HCl; 1 mM EDTA; 0.7% SDS) and treated with 400 µg/Ml of proteinase K at 50° C. for 1 hour. Subsequently, genomic DNA was extracted from the cell suspension by phenol/chloroform extraction and ethanol precipitation according to the conventional method in the art.

In the PCR amplification, the extracted genomic DNA was employed as a template DNA. As primer pairs, the synthetic nucleotides of SEQ ID NOs: 3 and 4 were employed to obtain DNA fragments containing: HGF gene fragment 2 (HGF-F2), SEQ ID NOs: 3 and 5; HGF-F3, SEQ ID NOs: 6 and 7; HGF-F5, SEQ ID NOs: 8 and 7; HGF-F7, SEQ ID NOs: 9 and 7; HGF-F8, SEQ ID NOs: 10 and 7; HGF-F6, respectively (FIG. 1). The PCR amplification mixture was prepared by mixing 1 µl of template DNA, 1 µl each of primer (10 pmol/µl), 10 µl of dNTP (10 mM), 3.5 unit of Expand High Fidelity enzyme (Gibco BRL, USA) and 10 µl of enzyme buffer solution and adjusted to a final volume of 100 µl with distilled water. 30 cycles of the PCR amplification was carried out, each cycle consisting of 1 min at 94° C., 1 min at 55° C. and 30 sec at 72° C. The primers used herein and the amplified gene fragments obtained therefrom are shown in Table 1.

TABLE 1

| 5' primer | 3' primer | Amplified fragment |
|---|---|---|
| gHGF3 (SEQ ID NO: 3) | gHGF4 (SEQ ID NO: 4) | HGF gene fragment 2 (HGF-F2) |
| gHGF3 (SEQ ID NO: 3) | gHGF10 (SEQ ID NO: 5) | HGF gene fragment 3 (HGF-F3) |
| gHGF5 (SEQ ID NO: 6) | gHGF7 (SEQ ID NO: 7) | HGF gene fragment 5 (HGF-F5) |
| gHGF12 (SEQ ID NO: 8) | gHGF7 (SEQ ID NO: 7) | HGF gene fragment 7 (HGF-F7) |
| gHGF13 (SEQ ID NO: 9) | gHGF7 (SEQ ID NO: 7) | HGF gene fragment 8 (HGF-F8) |
| gHGF6 (SEQ ID NO: 10) | gHGF7 (SEQ ID NO: 7) | HGF gene fragment 6 (HGF-F6) |

The amplified HGF-F2 comprised the sequence ranging from 392 to 2247 of human HGF cDNA prototype (HGF-X1; composed of exons 1 to 4-intron 4-exons 5 to 18) of SEQ ID NO: 2; HGF-F3, the sequence ranging from 392 to 727; HGF-5, the sequence ranging from 2229 to 5471; HGF-F6, the sequence ranging from 5117 to 5471; HGF-F7, the sequence ranging from 3168 to 5471; and HGF-F8, the sequence ranging from 4168 to 5471.

Figure 2:
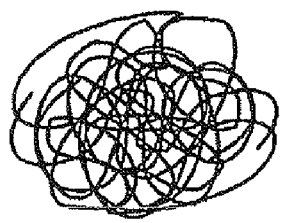
FIG. 2: a process for cloning gene fragments from HepG2 genomic DNA.

The amplified HGF gene fragments were each inserted into the multiple cloning site of pGEM-T easy vector (Promega, Wis., USA) to obtain pGEM-T easy-HGF-F2, pGEM-T easy-HGF-F3, pGEM-T easy-HGF-F5, pGEM-T easy-HGF-F6, pGEM-T easy-HGF-F7 and pGEM-T easy-HGF-F8, respectively (FIG. 2). The nucleotide sequences of the amplified HGF gene fragments were confirmed by a sequence analysis.

(2) Cloning of HGF Gene Fragments Obtained from cDNA

In the PCR amplification, human placenta cDNA (Clontech, Calif., USA) was employed as a template DNA under the same condition as described in Example 1. As primer pairs, the synthetic oligonucleotides of SEQ ID NOs: 11 and 12, and SEQ ID NOs: 13 and 14 were employed to obtain DNA fragments containing HGF-F1 and HGF-F4, respectively. Further, DNA fragments containing cDNAs of HGF gene (cHGF) and deleted HGF gene (dHGF) were amplified by PCR using synthetic oligonucleotides of SEQ ID NOs: 15 and 16 as a primer pair, respectively. dHGF is a HGF gene with deletion of 5 base sequences.

The primers used herein and the amplified gene fragments obtained therefrom are shown in Table 2.

TABLE 2

| 5' primer | 3' primer | Amplified fragment |
|---|---|---|
| gHGF1 (SEQ ID NO: 11) | gHGF2 (SEQ ID NO: 12) | HGF gene fragment 1 (HGF-F1) |
| gHGF8 (SEQ ID NO: 13) | gHGF9 (SEQ ID NO: 14) | HGF gene fragment 4 (HGF-F4) |
| cHGF5 (SEQ ID NO: 15) | cHGF3 (SEQ ID NO: 16) | HGF gene cDNA (cHGF) dHGF gene cDNA (dHGF) |

The amplified HGF-F1 and HGF-F4 comprised the nucleotide sequences ranging from 1 to 402 and from 6533 to 7113 of SEQ ID NO: 2 of human HGF cDNA prototype, respectively. HGF gene cDNA comprised the nucleotide sequence ranging from 1 to 2184 of SEQ ID NO: 1 of human HGF gene, and dHGF gene cDNA has the same sequence as HGF gene cDNA except for the deletion of the sequence ranging from 483 to 495.

Figure 3:
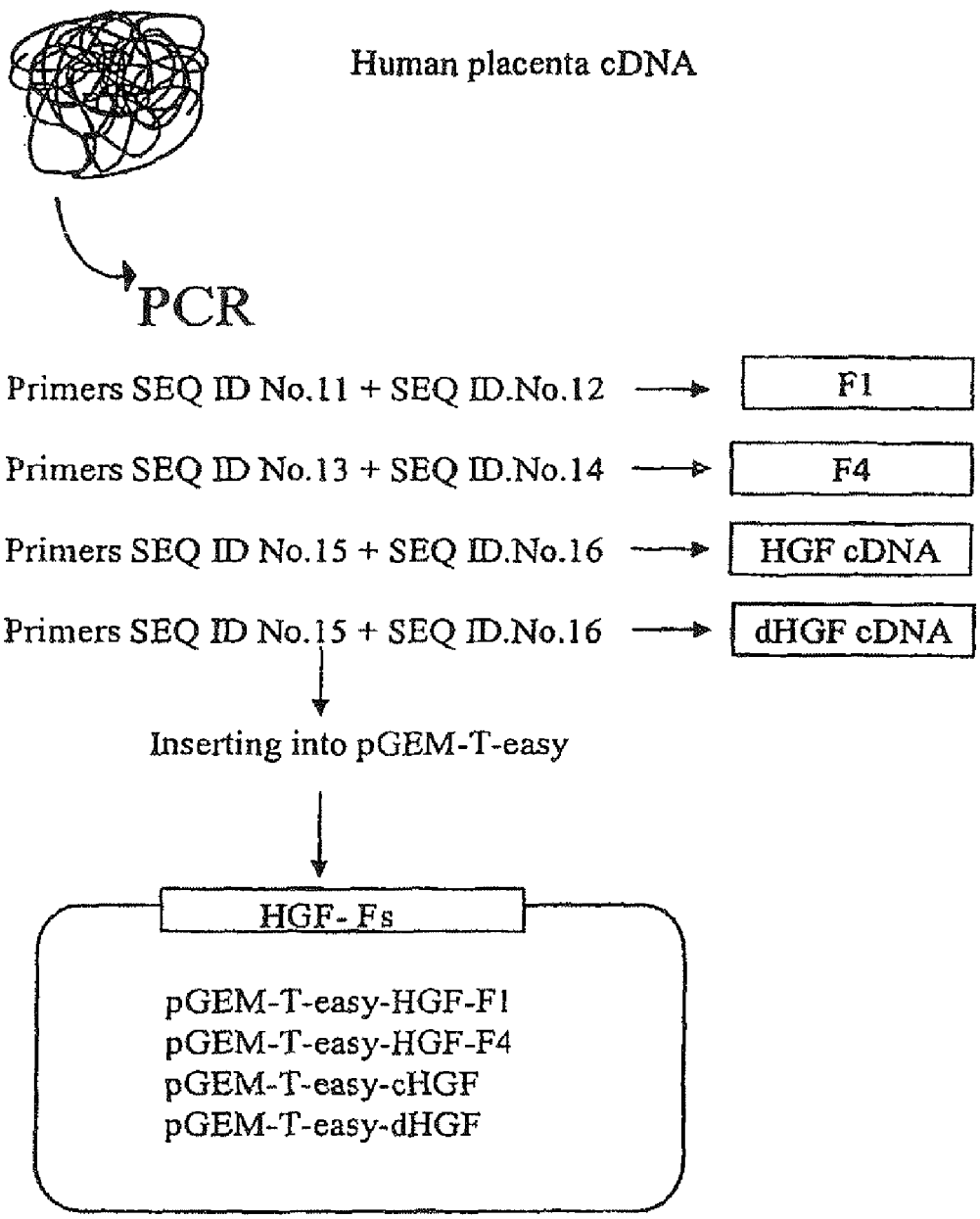
FIG. 3: a process for cloning gene fragments from human placenta cDNA.

The amplified fragments of HGF gene were each inserted into the multiple cloning site of pGEM-T easy vector (Promega, Wis., USA) to obtain pGEM-T easy-HGF-F1, pGEM-T easy-HGF-F4, pGEM-T easy-cHGF and pGEM-T easy-dHGF, respectively (FIG. 3). The nucleotide sequences of the human HGF gene fragments, HGF gene cDNA and dHGF gene cDNA were confirmed by sequence analyses.

(3) Preparation of Hybrid HGF Gene Constructs

Figure 4A:
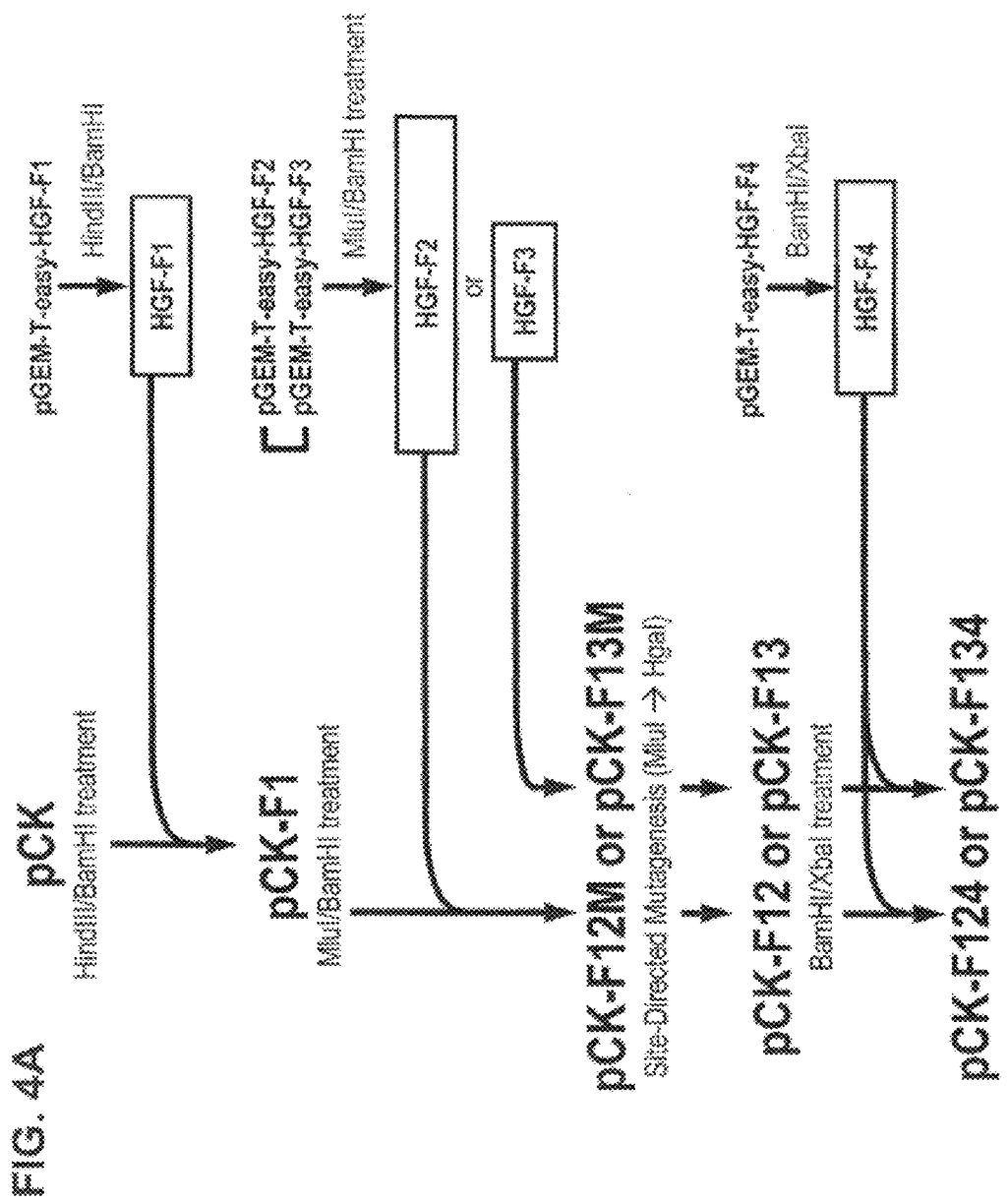
FIGS. 4A and 4B: processes for preparing expression vectors pCK-HGF-X.
Figure 4B:
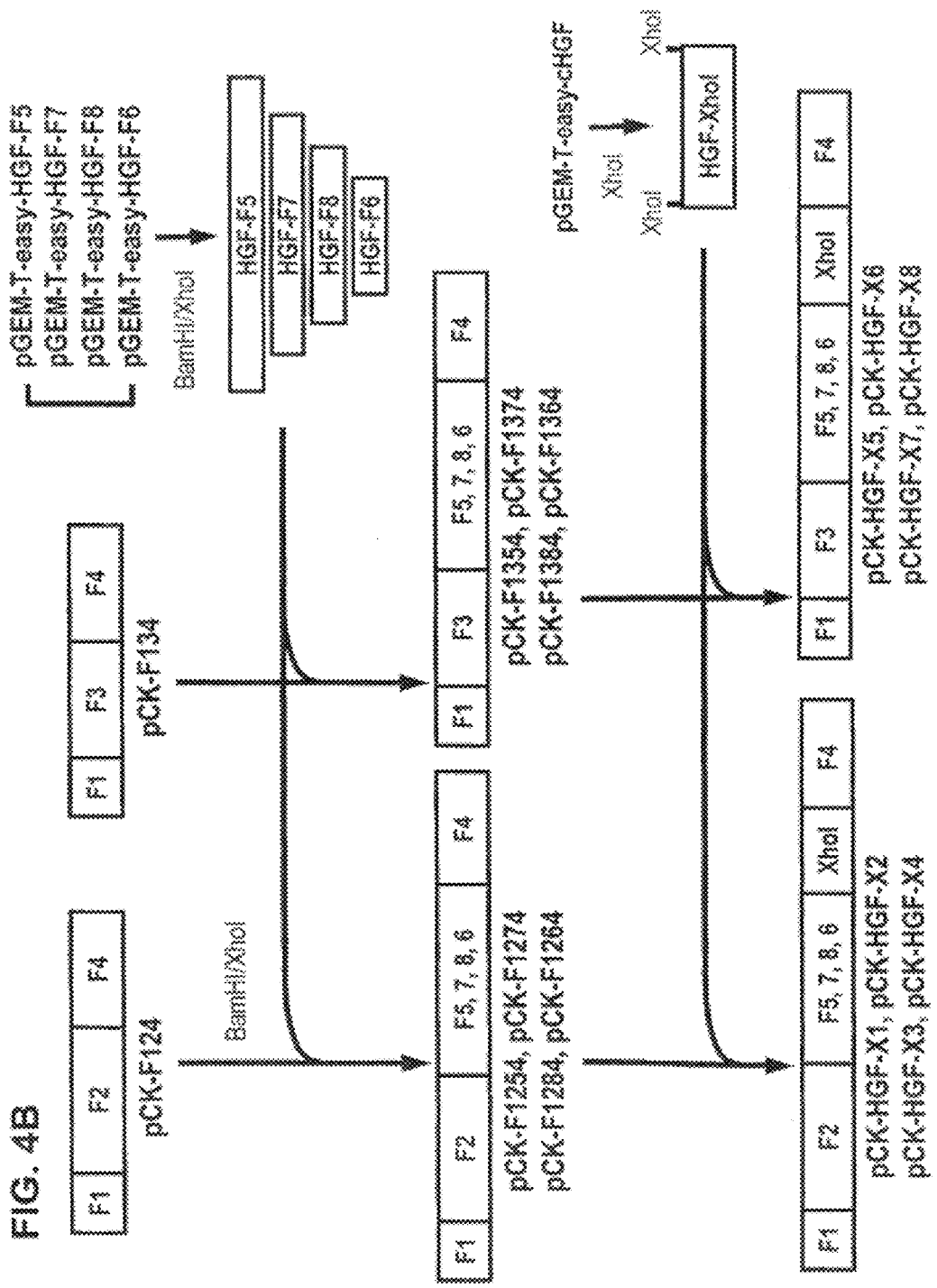

Hybrid HGF gene constructs of genomic DNA and cDNA were prepared by combining the fragments of HGF gene cloned in steps (1) and (2) as follows (FIGS. 4A and 4B).

Plasmid pGEM-T-easy-HGF-F1 was treated with HindIII/BamHI to obtain HGF-F1. Plasmid pCK (see PCT International Publication NO: WO/0040737) was treated with HindIII/BamHI, and HGF-F1 was inserted thereinto to obtain pCK-F1. And then, plasmids pGEM-T-easy-HGF-F2 and pGEM-T-easy-HGF-F3 were treated with MluI/BamHI to obtain HGF-F2 and HGF-F3, respectively. pCK-1 was treated with MluI/BamHI, and then HGF-F2 and HGF-F3 were inserted thereinto to obtain pCK-F12M and pCKF13M. The MluI restriction site of vectors pCK-F12M and pCK-F13M was substituted with an HgaI restriction site by employing a site-directed mutagenesis kit (Stratagene, CA, USA) to obtain pCK-F12 and pCK-F13, respectively.

Further, plasmid pGEM-T-easy-HGF-F4 was treated with BamHI/XbaI to obtain HGF-F4. pCK-F12 and pCK-F13 were treated with BamHI/XbaI, and HGF-F4 was inserted thereinto to obtain pCK-F124 and pCK-F134, respectively. And then, plasmids pGEM-T-easy-HGF-F5, pGEM-T-easy-HGF-F6, pGEM-T-easy-HGF-F7 and pGEM-T-easy-HGF-F8 were treated with BamHI/XhoI to obtain HGF-F5, HGF-F6, HGF-F7 and HGF-F8, respectively. pCK-F124 and pCK-F134 were treated with BamHI/XhoI, and then HGF-F5, HGF-F6, HGF-F7 and HGF-F8 were inserted thereinto to obtain pCK-F1254 and pCK-F1264, pCK-F1274, pCK-F1284, pCK-F1354, pCK-F1364, pCK-F1374 and pCK-F1384, respectively.

Figure 5:
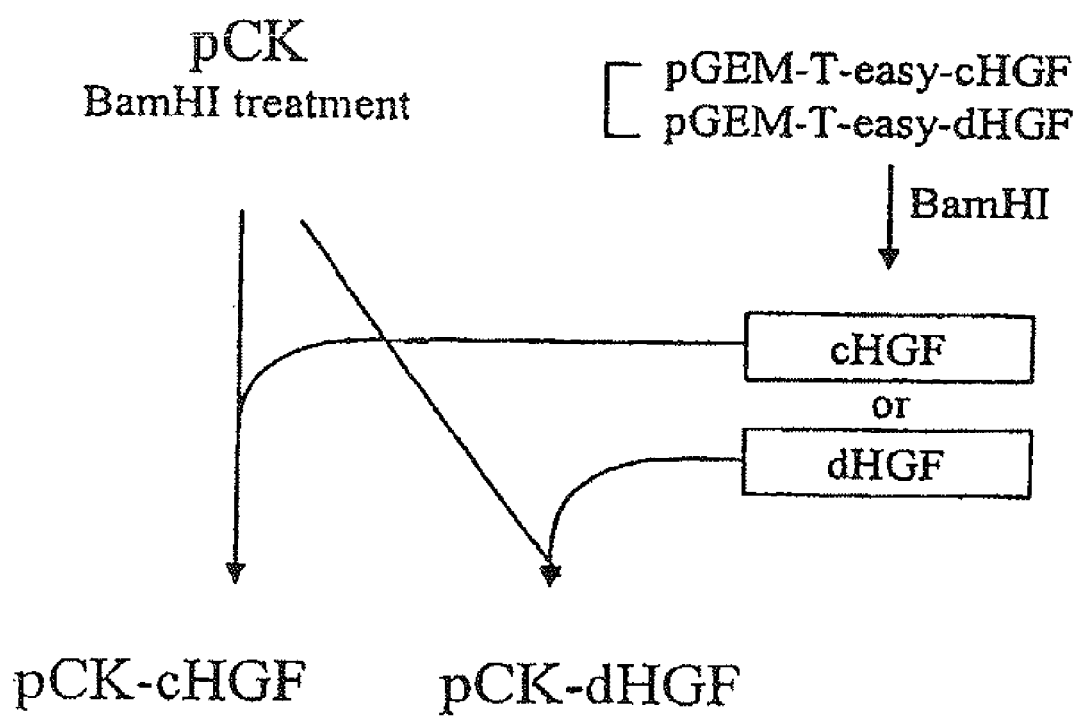
FIG. 5: a process for preparing expression vectors pCK-cHGF and pCK-dHGF.

And then, pGEM-T easy-cHGF was treated with XhoI to obtain cDNA fragment of HGF gene (HGF-XhoI) of about 1100 bp. Then, HGF-XhoI was inserted into pCK-F1254, pCK-F1264, pCK-F1274, pCK-F1284, pCK-F1354, pCK-F1364, pCK-F1374 and pCK-F1384 to obtain pCK-HGF-X1, pCK-HGF-X2, pCK-HGF-X3, pCK-HGF-X4, pCK-HGF-X5, pCK-HGF-X6, pCK-HGF-X7 and pCK-HGF-X8, respectively. On the other hand, pGEM-T easy-cHGF and pGEM-T easy-dHGF were treated with BamHI to obtain HGF gene cDNA and dHGF gene cDNA. Then, HGF gene cDNA and dHGF gene cDNA were inserted into the BamHI restriction site of pCK to obtain pCK-cHGF and pCK-dHGF, respectively (FIG. 5).

(4) Preparation of an Expression Vector Containing a Hybrid HGF Gene Construct

Figure 6:
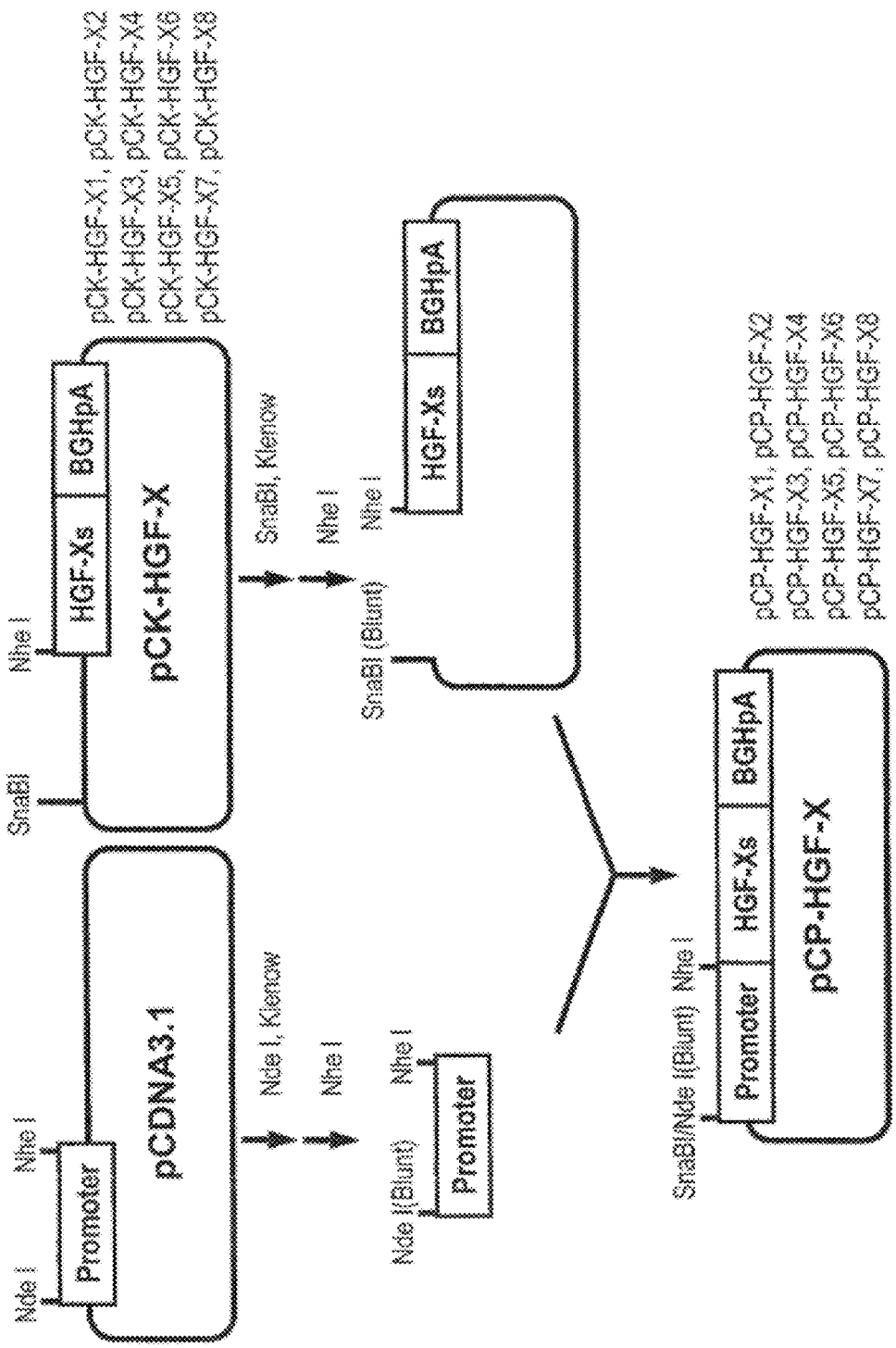
FIG. 6: a process for preparing expression vectors pCP-HGF-X family.

Plasmid pcDNA3.1 (Invitrogen, USA) was digested with NdeI, treated with the Klenow fragment to build blunt ends, and then digested with NheI to obtain a DNA fragment containing human cytomegalovirus promoter. Plasmids pCK-HGF-X1, pCK-HGF-X2, pCK-HGF-X3, pCK-HGF-X4, pCK-HGF-X5, pCK-HGF-X6, pCK-HGF-X7 and pCK-HGF-X8 were digested with SnaBI, treated with the Klenow fragment to make blunt ends and digested with NheI, and then the above DNA fragment containing human cytomegalovirus promoter was inserted thereinto to obtain pCP-HGF-X1, pCP-HGF-X2, pCP-HGF-X3, pCP-HGF-X4, pCP-HGF-X5, pCP-HGF-X6, pCP-HGF-X7 and pCP-HGF-X8, respectively (FIG. 6).

Figure 7:
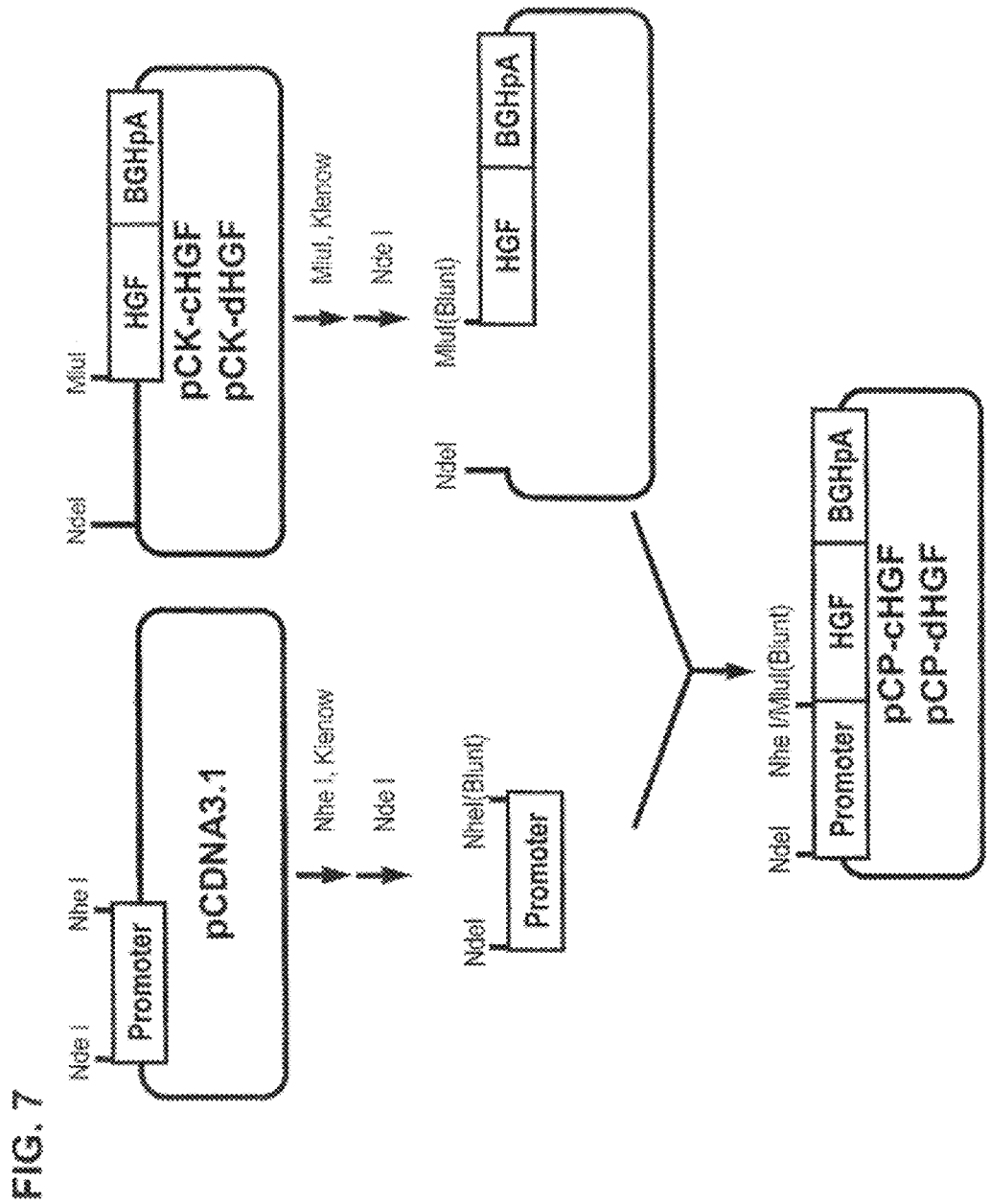
FIG. 7: a process for preparing expression vectors pCP-cHGF and pCP-dHGF.

Plasmid pcDNA3.1 (Invitrogen, USA) was digested with NheI, treated with the Klenow fragment to make blunt ends and digested with NdeI to obtain the DNA fragment containing human cytomegalovirus promoter. pCK-cHGF and pCK-dHGF were digested with MluI, treated with the Klenow fragment to make blunt ends and digested with NdeI, and then the above DNA fragment containing human cytomegalovirus promoter was inserted thereinto to obtain pCP-cHGF and pCP-dHGF, respectively (FIG. 7).

EXAMPLE 2

Examination of the Expression Efficiency of Hybrid HGF Gene Construct and the Coexpression of HGF/dHGF Studies were conducted to examine whether the hybrid HGF gene constructs (HGF-X1 to HGF-X8) obtained in Example 1 can simultaneously express HGF and dHGF and whether there is any difference in the gene expression level between hybrid HGF gene constructs and HGF cDNA.

(1) Gene Expression Efficiency

First, 5 µg of pCP-HGF-X2, pCP-HGF-X3, pCP-HGF-X6, pCP-HGF-X7 and pCP-HGF-X8 were transfected into $5 \times 10^6$ cells of 293 cell (ATCC CRL 1573) together with 0.5 µg of DONAI-LacZ (TAKARA SHUZO, Japan) DNA using FuGENE6 (Gibco BRL, MD, USA), according to the manufacturer's instructions. At this time, 5 µg each of pCP-cHGF and pCP-dHGF were used as controls, and DONAI-LacZ DNA was used to calibrate the infection efficiency. 3 hours after transfection, cells were re-fed with a fresh medium and further cultured for 48 hours. The culture solution thus obtained was divided into two parts. One part of the 293 cell culture solution was subjected to RNA extraction, and the other, to measurement of LacZ activity. The LacZ activity was measured using an activity measuring kit (Stratagene, Calif., USA) according to the manufacturer's instructions.

Figure 8:
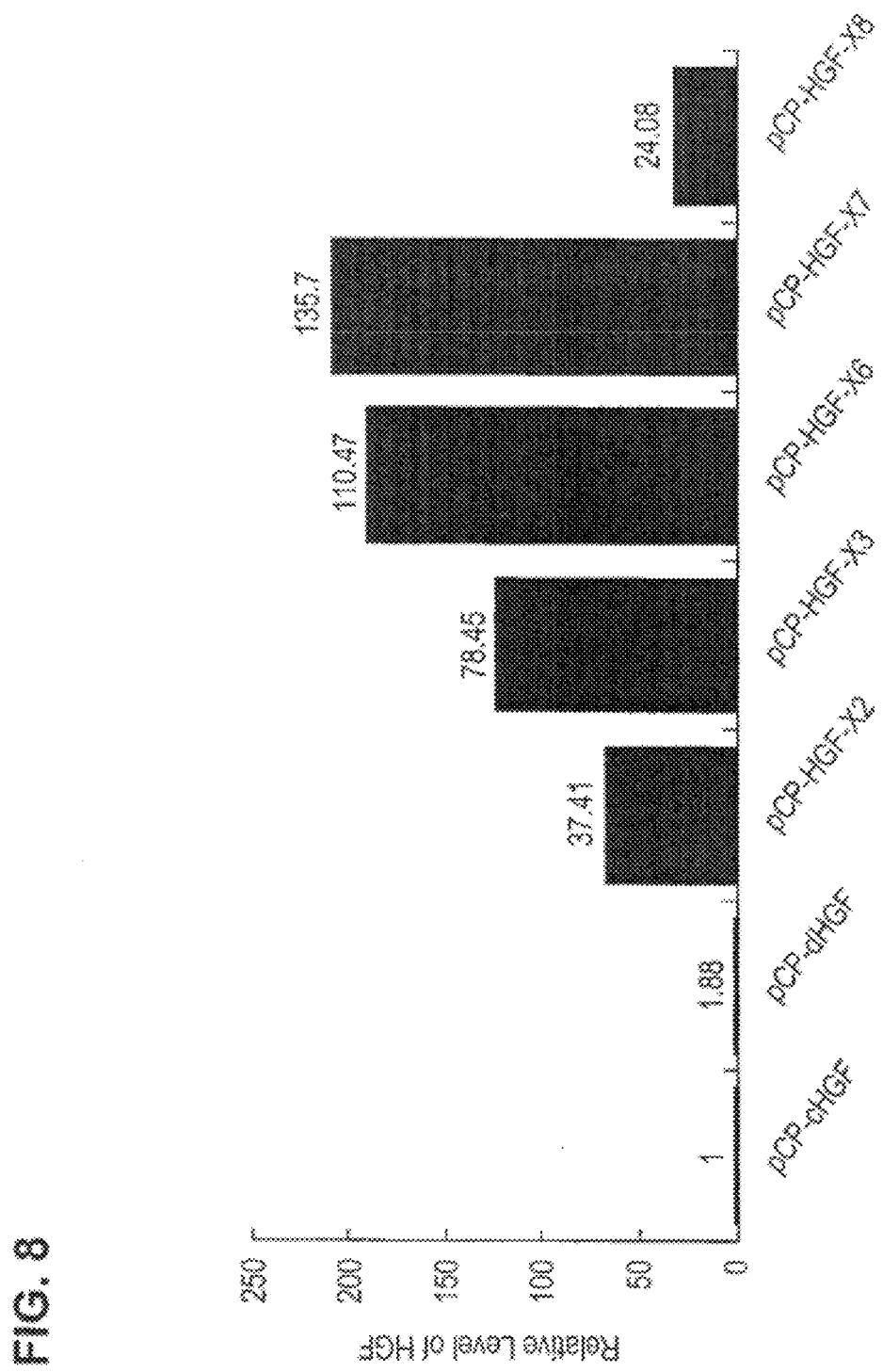
FIG. 8: gene expression levels of pCP-cHGF, pCP-dHGF and pCP-HGF-X.

In order to compare the gene expression levels, the amount of HGF in the cell culture was measured by an enzyme-linked immunosorbent assay kit (ELISA, R&D System, MN, USA). After calibrating the infection efficiency by the measured LacZ activity, the expression level of HGF-X gene was found to be from 20 to 150-fold higher than those of HGF cDNA and dHGF cDNA (FIG. 8). HGF-X7, in particular, showed the highest gene expression level.

(2) Coexpression of HGF and dHGF

In order to examine coexpression of HGF and dHGF from hybrid HGF gene constructs, total cellular RNAs were extracted from the transfected 293 cells using the Trizol method (Trizol; Gibco BRL, USA) and subjected to RT-PCR to obtain cDNA. Then, using cDNA as a template DNA, PCR amplification was carried out using synthetic oligonucleotides of SEQ ID NOs: 17 and 18 as a primer pair. The PCR amplification mixture was prepared by mixing 1 µl of the template DNA, 1 µl each of the primer (10 pmol/µl), 10 µl of dNTP (10 mM), 3.5 unit of Taq polymerase (TAKARA SHUZO, Japan) and 10 µl of enzyme buffer solution and adjusted to a final volume of 100 µl with distilled water. 30 cycles of PCR amplification was conducted, each cycle consisting of 1 min at 94° C., 1 min at 55° C., and 90 sec at 72° C.

The amplified PCR products corresponded to the boundary region between exons 4 and 5 of HGF gene; HGF gene cDNA of 142 bp and dHGF gene cDNA of 127 bp, respectively. With no splicing, the PCR product of at least 1 kb in length was amplified; and if alternative splicing occurred, HGF gene cDNA of 142 bp and dHGF gene cDNA of 127 bp were simultaneously synthesized and amplified. The amplified PCR products were distinguished by electrophoresis on a 12% polyacrylamide gel.

Figure 9:
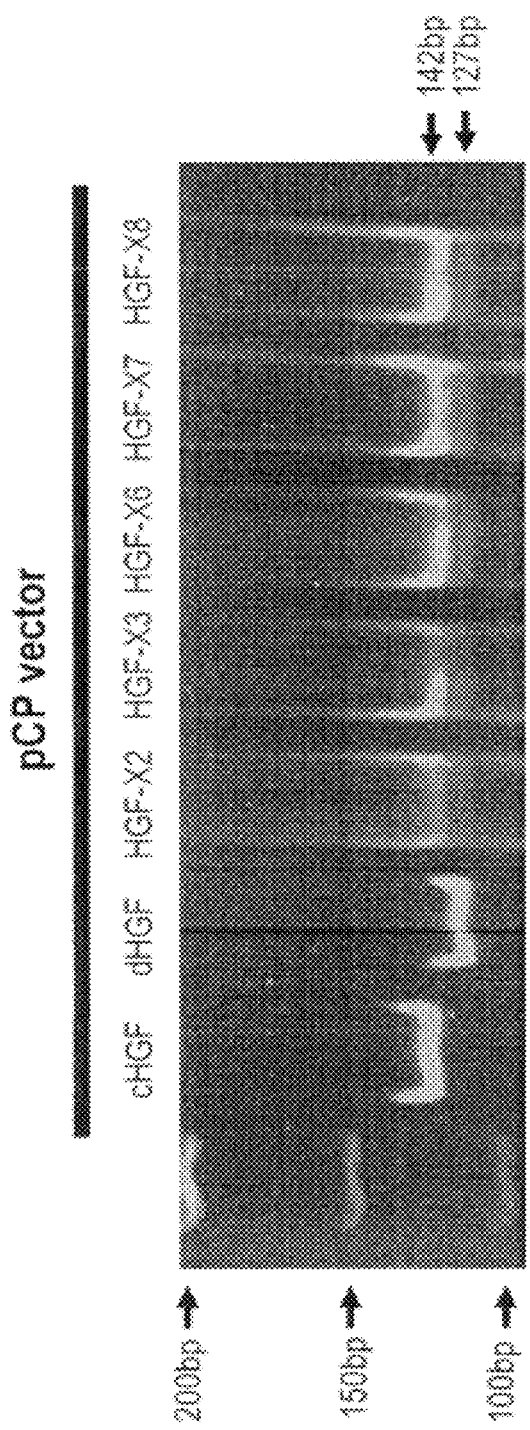
FIG. 9: gene expression patterns of pCP-cHGF, pCP-dHGF and pCP-HGF-X observed by electrophoresis on 12% polyacrylamide gel.

As shown in FIG. 9, while the bands of 142 bp and 127 bp were detected in the lanes loading HGF gene cDNA and dHGF gene cDNA, respectively, both bands of 142 bp and 127 bp were detected in the lanes loading HGF-X. The above results suggest that HGF and dHGF are simultaneously expressed from hybrid HGF-X gene constructs of the present invention.

EXAMPLE 3

Comparison of Expression Levels of HGF-X7, HGF Gene cDNA and dHGF Gene cDNA (In Vivo)

100 μg each of pCP-HGF-X7, pCP-cHGF and pCP-dHGF were injected into the interior tibial muscle of the hind limb of mice with an insulin syringe. After 5 days, the mice were sacrificed and the muscles around the injection spot were removed and smashed in a protein extraction buffer (25 mM Tris-HCl (pH 7.4), 50 mM NaCl, 0.5% Na-deoxycholate, 2% NP-40, 0.2% SDS) to separate total proteins. The amount of the total proteins was measured with a DC protein analysis kit (Bio-Rad Laboratories, CA, USA) and the amount of expressed HGF was determined with an ELISA kit (R&D System) according to the manufacturer's instruction.

Figure 10:
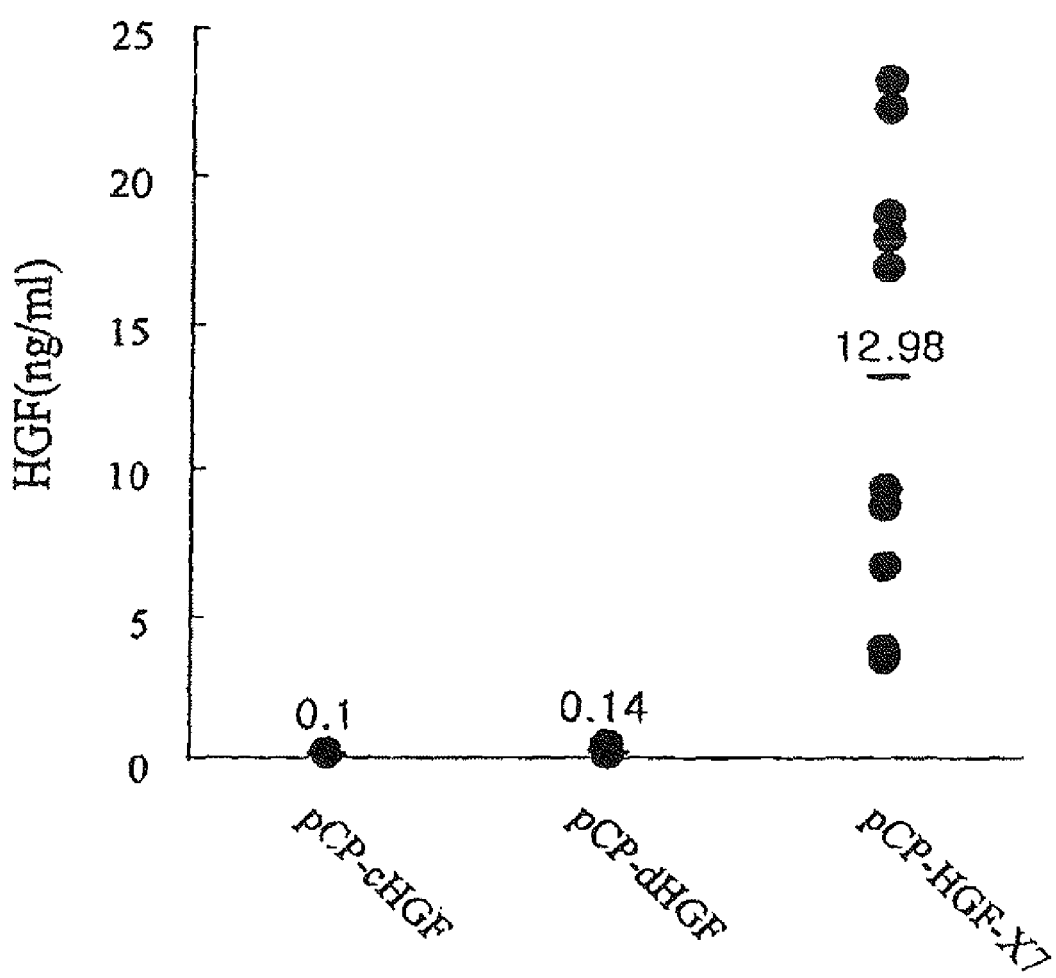
FIG. 10: gene expression levels of pCP-cHGF, pCP-dHGF and pCP-HGF-X7, in vivo.

As can be seen from the result shown in FIG. 10, the amount of HGF expressed from HGF-X7 is 250-fold higher than that from HGF gene cDNA or dHGF gene cDNA.

Together with the result of the experiment of Example 2 (in vivo), this result demonstrates that the expression efficiency of HGF-X gene is much superior to those of HGF gene cDNA or dHGF gene cDNA.

EXAMPLE 4

Gene Therapy Employing HGF-X7 in a Rabbit Ischemic Hind Limb Model

In order to examine whether HGF-X7 gene is effective in the treatment of ischemic hind limb disease, gene therapy was carried out on a rabbit ischemic hind limb model as follows.

A rabbit ischemic hind limb model, which is a standard animal model for the ischemic limb disease, was prepared by the method described by Takeshita et al., *Journal of Clinical Investigation* 93:662 (1994). At the day before operation (day 0), each of 30 white rabbits from New Zealand (male, from 3.8 to 4.2 kg) was intramuscularly injected with 5 mg/kg of xylazine and, then, anesthetized by an intramuscular injection of 50 mg/kg of ketamine. Subsequently, the left femoral region of the rabbit was incised and all branches of the femoral artery were separated and tied. The region from the proximal part to the branching point of the saphenous and popliteal arteries was incised to prepare the model. After the operation, 15 mg/kg/day of cefazolin was injected intramuscularly for 5 days and 0.3 mg/day of morphin, for 10 days. 10 days after the operation (day 10), angiography was carried out for the left hind limb where the ischemia was induced, and the degree of arteriogenesis was recorded as a basal level. The rabbits were randomly divided into two groups and injected at four sites in the femoral muscle with 500 μg of plasmid pCP-HGF-X7 (experimental group) or 500 μg of plasmid pCP (control), respectively. 40 days after the operation (day 40), angiography was carried out again for the left hind limb and the degree of arteriogenesis at the arteriole level was determined and compared to that of day 10.

Figure 11:
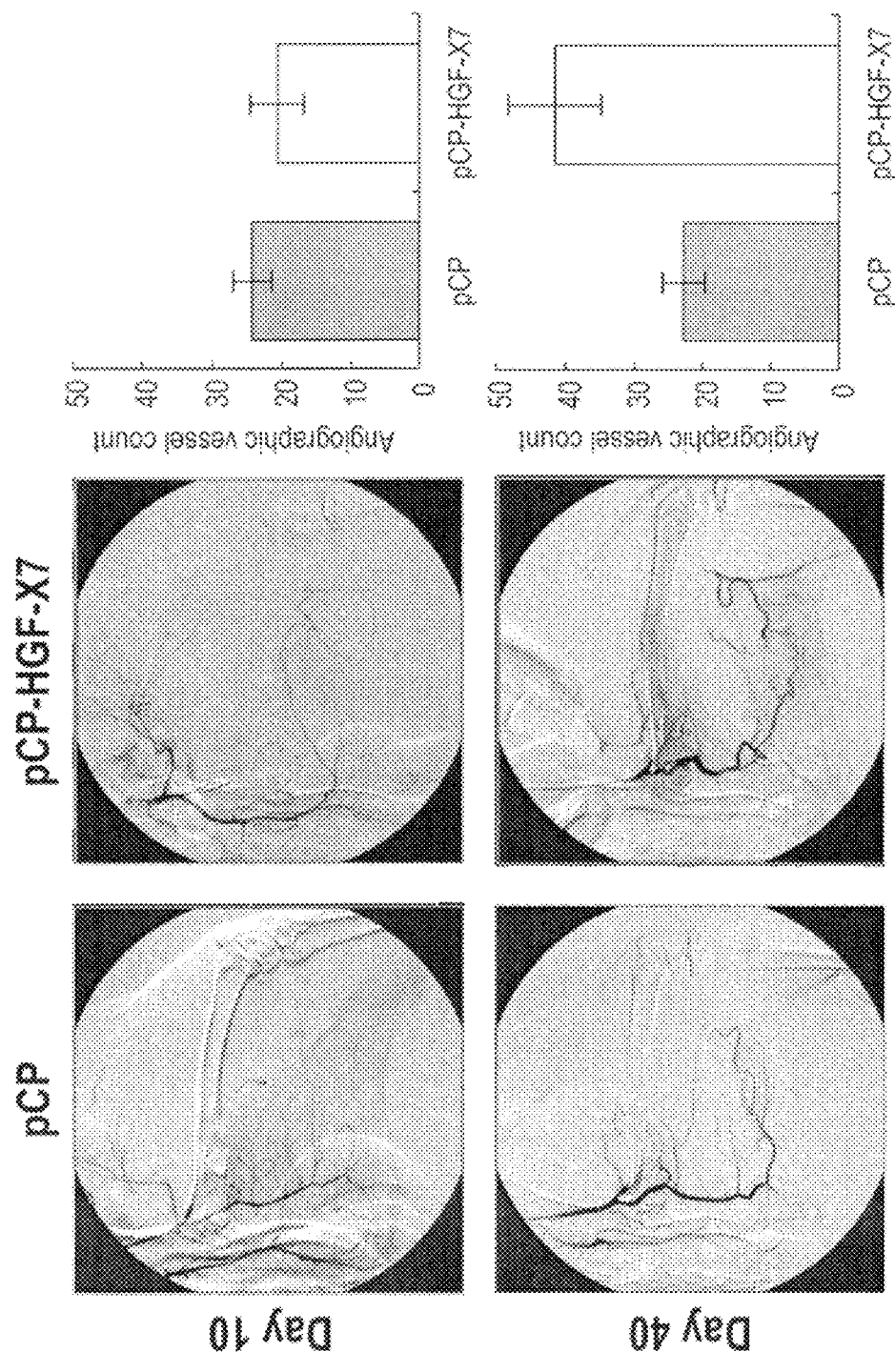
FIG. 11: angiographic vessel count of two groups of rabbits which were subject to administrating pCP and pCP-HGF-X7, respectively.

As can be seen from the result in FIG. 11, the degree of angiogenesis was significantly enhanced in the experimental group administered with pCP-HGF-X7 as compared with the pCP-administered control group.

This result demonstrates that HGF-X7 gene can be effectively used in the gene therapy of an ischemic disease.

While the invention has been described with respect to the above specific embodiments, it should be recognized that various modifications and changes may be made to the invention by those skilled in the art which also fall within the scope of the invention as defined by the appended claims.

What is claimed is:

1. A method of treating an ischemic limb disease in a subject comprising intramuscularly administering to the ischemic limb of said subject a hybrid Hepatocyte Growth Factor (HGF) construct comprising:
(a) a first cDNA which has the same sequence as exons 1-4 of the human HGF gene wherein said exons 1-4 are arranged in sequential order without an intron therebetween, or degenerates thereof which do not alter the amino acid sequence encoded by said first cDNA,
(b) a polynucleotide that has the same sequence as intron 4 of a HGF gene or a fragment thereof, and
(c) a second cDNA which has the same sequence as exons 5-18 of the human HGF gene wherein said exons 5-18 are arranged in sequential order without an intron therebetween, or degenerates thereof which do not alter the amino acid sequence encoded by said second cDNA,
wherein (b) is located between (a) and (c) and the HGF construct simultaneously encodes two heterotypes of human HGF;
wherein said administration treats the ischemic limb disease in said subject.

2. The method of claim 1, wherein the polynucleotide of (b) has the same sequence as the full intron 4 of the human HGF gene.

3. The method of claim 2, wherein said hybrid HGF construct comprises a nucleotide sequence comprising SEQ ID NO: 2.

4. The method of claim 1, wherein the polynucleotide of (b) has the same sequence as a fragment of intron 4 of the human HGF gene.

5. The method of claim 4, wherein said hybrid HGF construct comprises SEQ ID NO: 19.

6. The method of claim 4, wherein said hybrid HGF construct comprises SEQ ID NO: 20.

7. The method of claim 4, wherein said hybrid HGF construct comprises SEQ ID NO: 21.

8. The method of claim 1, wherein said hybrid HGF construct is comprised in a vector.

9. The method of claim 8, wherein said vector further comprises one or more sequences for regulating expression, a self-replication sequence, or a secretory signal.

10. The method of claim 8, wherein said vector comprising said HGF construct is selected from the group consisting of: pCK-HGF-X1, pCK-HGF-X2, pCK-HGF-X3, pCK-HGF-X4, pCK-HGF-X5, pCK-HGF-X6, pCK-HGF-X7, pCK-HGF-X8, pCP-HGF-X1, pCP-HGF-X2, pCP-HGF-X3, pCP-HGF-X4, pCP-HGF-X5, pCP-HGF-X6, pCP-HGF-X7 and pCP-HGF-X8.

11. The method of claim 1, wherein said hybrid HGF construct is administered by direct injection.

12. A method of treating an ischemic limb disease in a subject comprising intramuscularly administering to the ischemic limb of said subject a hybrid Hepatocyte Growth Factor (HGF) construct comprising a polynucleotide having a nucleotide sequence not less than 90% identical to a sequence selected from the group consisting of SEQ ID NO: 2, SEQ ID NO: 19, SEQ ID NO: 20, and SEQ ID NO: 21, wherein the polynucleotide having said nucleotide sequence simultaneously encodes two heterotypes of human HGF, wherein said administration treats the isehernic limb disease in said subject.

13. The method of claim 12, wherein said nucleotide sequence is not less than 95% identical to SEQ ID NO:2.

14. The method of claim 12, wherein said nucleotide sequence is not less than 95% identical to SEQ ID NO: 19.

15. The method of claim 12, wherein said nucleotide sequence is not less than 95% identical to SEQ ID NO: 20.

16. The method of claim 12, wherein said nucleotide sequence is not less than 95% identical to SEQ ID NO: 21.

* * * * *

SEQUENCE LISTING

```
<160> NUMBER OF SEQ ID NOS: 21

<210> SEQ ID NO 1
<211> LENGTH: 2187
<212> TYPE: DNA
<213> ORGANISM: Homo sapiens

<400> SEQUENCE: 1
atgtgggtga ccaaactcct gccagccctg ctgctgcagc atgtcctcct gcatctcctc        60
ctgctcccca tcgccatccc ctatgcagag ggacaaagga aagaagaaa tacaattcat       120 gaattcaaaa aatcagcaaa gactacccta atcaaaatag atccagcact gaagataaaa       180
accaaaaaag tgaatactgc agaccaatgt gctaatagat gtactaggaa taaaggactt       240
ccattcactt gcaaggcttt tgtttttgat aaagcaagaa aacaatgcct ctggttcccc       300
ttcaatagca tgtcaagtgg agtgaaaaaa gaatttggcc atgaatttga cctctatgaa       360
aacaaagact acattagaaa ctgcatcatt ggtaaaggac gcagctacaa gggaacagta       420
tctatcacta agagtggcat caaatgtcag ccctggagtt ccatgatacc acacgaacac       480
```

| | |
|---|---|
| agcttttgc cttcgagcta tcggggtaaa gacctacagg aaaactactg tcgaaatcct | 540 |
| cgaggggaag aagggggacc ctggtgtttc acaagcaatc cagaggtacg ctacgaagtc | 600 |
| tgtgacattc ctcagtgttc agaagttgaa tgcatgacct gcaatgggga gagttatcga | 660 |
| ggtctcatgg atcatacaga atcaggcaag atttgtcagc gctgggatca tcagacacca | 720 |
| caccggcaca aattcttgcc tgaaagatat cccgacaagg gctttgatga taattattgc | 780 |
| cgcaatcccg atggccagcc gaggccatgg tgctatactc ttgaccctca cacccgctgg | 840 |
| gagtactgtg caattaaaac atgcgctgac aatactatga atgacactga tgttcctttg | 900 |
| gaaacaactg aatgcatcca aggtcaagga aaggctaca gggcactgt caataccatt | 960 |
| tggaatggaa ttccatgtca gcgttgggat tctcagtatc ctcacgagca tgacatgact | 1020 |
| cctgaaaatt tcaagtgcaa ggacctacga gaaaattact gccgaaatcc agatgggtct | 1080 |
| gaatcaccct ggtgttttac cactgatcca acatccgag ttggctactg ctcccaaatt | 1140 |
| ccaaactgtg atatgtcaca tggacaagat tgttatcgtg gaatggcaa aaattatatg | 1200 |
| ggcaacttat cccaaacaag atctggacta acatgttcaa tgtgggacaa gaacatggaa | 1260 |
| gacttacatc gtcatatctt ctgggaacca gatgcaagta agctgaatga gaattactgc | 1320 |
| cgaaatccag atgatgatgc tcatggaccc tggtgctaca cgggaaatcc actcattcct | 1380 |
| tgggattatt gccctatttc tcgttgtgaa ggtgatacca cacctacaat agtcaattta | 1440 |
| gaccatcccg taatatcttg tgccaaaacg aaacaattgc gagttgtaaa tgggattcca | 1500 |
| acacgaacaa acataggatg gatggttagt ttgagataca gaaataaaca tatctgcgga | 1560 |
| ggatcattga taaggagag ttgggttctt actgcacgac agtgtttccc ttctcgagac | 1620 |
| ttgaaagatt atgaagcttg gcttggaatt catgatgtcc acggaagagg agatgagaaa | 1680 |
| tgcaaacagg ttctcaatgt tcccagctg gtatatggcc ctgaaggatc agatctggtt | 1740 |
| ttaatgaagc ttgccaggcc tgctgtcctg gatgattttg ttagtacgat tgatttacct | 1800 |
| aattatggat gcacaattcc tgaaaagacc agttgcagtg tttatggctg gggctacact | 1860 |
| ggattgatca actatgatgg cctattacga gtggcacatc tctatataat gggaaatgag | 1920 |
| aaatgcagcc agcatcatcg agggaaggtg actctgaatg agtctgaaat atgtgctggg | 1980 |
| gctgaaaaga ttggatcagg accatgtgag ggggattatg gtggcccact tgtttgtgag | 2040 |
| caacataaaa tgagaatggt tcttggtgtc attgttcctg gtcgtggatg tgccattcca | 2100 |
| aatcgtcctg gtattttgt ccgagtagca tattatgcaa aatggataca caaaattatt | 2160 |
| ttaacatata aggtaccaca gtcatag | 2187 |

<210> SEQ ID NO 2
<211> LENGTH: 7113
<212> TYPE: DNA
<213> ORGANISM: Homo sapiens

<400> SEQUENCE: 2

| | |
|---|---|
| atgtgggtga ccaaactcct gccagccctg ctgctgcagc atgtcctcct gcatctcctc | 60 |
| ctgctcccca tcgccatccc ctatgcagag ggacaaagga aagaagaaa tacaattcat | 120 |
| gaattcaaaa aatcagcaaa gactacccta atcaaaatag atccagcact gaagataaaa | 180 |
| accaaaaaag tgaatactgc agaccaatgt gctaatagat gtactaggaa taaggacttt | 240 |
| ccattcactt gcaaggcttt tgttttgat aaagcaagaa acaatgcct ctggttcccc | 300 |
| ttcaatagca tgtcaagtgg agtgaaaaaa gaatttggcc atgaatttga cctctatgaa | 360 |
| aacaaagact acattagaaa ctgcatcatt ggtaaaggac gcagctacaa gggaacagta | 420 |

```
tctatcacta agagtggcat caaatgtcag ccctggagtt ccatgatacc acacgaacac      480
aggtaagaac agtatgaaga aaagagatga agcctctgtc ttttttacat gttaacagtc      540
tcatattagt ccttcagaat aattctacaa tcctaaaata acttagccaa cttgctgaat      600
tgtattacgg caaggtttat atgaattcat gactgatatt tagcaaatga ttaattaata      660
tgttaataaa atgtagccaa acaatatct taccttaatg cctcaatttg tagatctcgg       720
tatttgtgaa ataataacgt aaacttcgtt taaaaggatt cttcttcctg tctttgagaa      780
agtacggcac tgtgcagggg gagaggttga ttgtgaaaaa tcagaggtag atgagaatct      840
tactgagggc tgagggttct ttaaccttgg tggatctcaa cattggttgc acattaaaat      900
cacctgctgc aagcccttga cgaatcttac ttagaagatg acaacacaga acaattaaat      960
cagaatctct ggggagaata gggcaccagt atttttgag ctcccaccat gattccaaag      1020
tgcagccaaa tttgagaacc actgctaaaa gctcaagctt cagattgacc agcttttcca     1080
tctcacctat cgcctaaaga ccaaattgga taaatgtgtt cattacgaca gatgggtact     1140
atttaaagat gagtaaacac aatatactta ggctcgtcag actgagagtt ttaatcatca     1200
ctgaggaaaa acatagatat ctaatactga ctggagtatt agtcaaggct tatttcacac     1260
acaattttat cagaaaccaa agtagtttaa aacagctctc cccttattag taatgcattg     1320
gagggtttac tttaccatgt accttgctga gcactgtacc ttgttaatct catttacttg     1380
taatgagaac cacacagcgg gtagttttat tggttctatt ttacctacat gacaaaactg     1440
aagcataaaa acacttagta agttttcagt gtcatgcaca actaggaagt gacatggcca     1500
gaatataagc ccagtcacca tcactctata acctgcgctt ttaacaactt cagggcatga     1560
cacatttggc cggtcagtag aacccatgct gtgatttgtt tttgcagtgg tggtgatgac     1620
tgccttgttg aatccacttt ttattctatt ccatttggg gacacaattc tgcaagatga      1680
ttcttcatta ggaaacagag atgagttatt gaccaacaca gaaagaaaaa gagtttgttg     1740
ctccacactg ggattaaacc tatgatcttg gcctaattaa cactagctag taagtgtcca     1800
agctgatcat ctctacaaca tttcaataac agaaaacaac aattttcaaa attagttact     1860
tacaattatg tagaaatgcc tctaaaacac agtattttcc ttatattaca aaacaaaaa     1920 ttataattgg ttttgtcctc ttttgagagt ttgcatggtg ttactccctg catagtgaag     1980
aaaacatttt atttaagtag atggatctaa gtttttcatg aacaaaggaa tgacatttga     2040
aatcaatcct accctagtcc aggagaatgc attagattaa cctagtagag gtcttatttc     2100
accctgagtt ttctatgatc gtgattctct gctggaggag taattgtgaa atagatctct     2160
ctgggaactg gcttcctagt ccaatcagct ctttaccaa tgaacacttc cttgtgatat      2220
agatgtttat ggccgagagg atccagtata ttaataaaat cccttttgt attcaatgag      2280 ggaaacacat aattttcatc aattagcagc ttattggaat atctgcatga tggtttaaca     2340
cttttaagtg ttgactaaag attaatttta cagaaaatag aaaagaaat atgtttctgt     2400 ctggaggaat gatttattgt tgacccctaa attgaaatat tttactagtg cttaatgga      2460 aagatgatga aagatgatga aattaatgta gaagcttaac tagaaaatca ggtgacctga     2520
tatctacatc tgtatccttc attggccacc cagcattcat taatgaatca gatgatggaa     2580
tagatcaagt ttcctaggaa cacagtgaat attaaaagaa aacaagggaa gcctagcacc     2640
tagaagacct agtttatatt tcaaagtata tttggatgta acccaatttt aaacatttcc     2700
tcacttgtct ctcttaaagc cttgccaaca gcaaggacag agaaccaaaa atagtgtata     2760
tatgaataaa tgcttattac agaatctgct gactggcaca tgctttgtgt gtaatgggtt     2820
```

```
ctcataaaca cttgttgaat gaacacacat aagtgaaaga gcatggctag gcttcatccc    2880
ttggtcaaat atggggtgct aaagaaaagc aggggaaata cattgggaca ctaacaaaaa    2940
aaaacagtta atttaggtaa aagataaaat acaccacaga atgaagaaaa gagatgaccc    3000
agactgctct ttaaccttca tgtcctagag aggttttttga tatgaattgc attcagaatt   3060
gtggaaagga gcccatcttt tctcttcatt ttgattttat taactccaat ggggaattt    3120 tattcgtgtt ttggccatat ctactttga tttctacatt attctctctt cctttctacc    3180
tgtatttgtc ctaataaatt gttgacttat taattcacta cttcctcaca gctttttttt    3240
ggctttacaa atccactgga aaggtatatg ggtgtatcac tttgtgtatt tcggtgtgca    3300
tgtgtagagg ggacaaaaat cctctctcaa actataaata ttgagtattt gtgtattgaa    3360
catttgctat aactactagg tttcttaaat aatcttaata tataaaatga tatagaaaaa    3420
gggaaattat agttcgtatt attcatctaa gtgaagagat taaaacccag ggagtaaata    3480
aattgtctaa ggactaaggt tgtatactat ttaggtgata gatatggggc aaccgtatgg    3540 gtttttatgat taacaaataa acttctcacc actctaccat atcaactttt ccataaaaga    3600
gagctatagt attctttgct taaataaatt tgattagtgc atgacttctt gaaaacatat    3660
aaagcaaaag tcacatttga ttctatcaga aaagtgagta agccatggcc caaacaaaag    3720
atgcattaaa atattctgga atgatggagc taaaagtaag aaaaatgact ttttaaaaaa    3780
gtttactgtt aggaattgtg aaattatgct gaattttagt tgcattataa ttttttgtcag    3840 tcatacggtc tgacaacctg tcttatttct atttccccat atgaggaatg ctagttaagt    3900
atggatatta actattacta cttagatgca ttgaagttgc ataatatgga taatacttca    3960
ctggttccct gaaaatgttt agttagtaat aagtctctta cactatttgt tttgtccaat    4020
aatttatatt ttctgaagac ttaactctag aatacactca tgtcaaaatg aaagaatttc    4080
attgcaaaat attgcttggt acatgacgca tacctgtatt tgttttgtgt cacaacatga    4140
aaaatgatgg tttattagaa gtttcattgg gtaggaaaca catttgaatg gtatttacta    4200
agatactaaa atccttggac ttcactctaa ttttagtgcc atttagaact caaggtctca    4260
gtaaaagtag aaataaagcc tgttaacaaa acacaagctg aatattaaaa atgtaactgg    4320
attttcaaag aaatgtttac tggtattacc tgtagatgta tattctttat tatgatcttt    4380
tgtgtaaagt ctggcagaca aatgcaatat ctaattgttg agtccaatat cacaagcagt    4440 acaaagtat aaaaaagact tggccttttc taatgtgtta aaatacttta tgctggtaat    4500
aacactaaga gtagggcact agaaaatttta agtgaagata atgtgttgca gttactgcac    4560
tcaatggctt actattataa accaaaactg ggatcactaa gctccagtca gtcaaaatga    4620
tcaaaattat tgaagagaat aagcaattct gttctttatt aggacacagt agatacagac    4680
tacaaagtgg agtgtgctta ataagaggta gcatttgtta agtgtcaatt actctattat    4740
cccttggagc ttctcaaaat aaccatataa ggtgtaagat gttaaaggtt atggttacac    4800
tcagtgcaca ggtaagctaa taggctgaga gaagctaaat tacttactgg ggtctcacag    4860
taagaaagtg agctgaagtt tcagcccaga tttaactgga ttctgggctc tttattcatg    4920
ttacttcatg aatctgtttc tcaattgtgc agaaaaaagg gggctattta taagaaaagc    4980
aataaacaaa caagtaatga tctcaaataa gtaatgcaag aaatagtgag atttcaaaat    5040
cagtggcagc gatttctcag ttctgtccta agtggccttg ctcaatcacc tgctatcttt    5100
tagtggagct ttgaaattat gtttcagaca acttcgattc agttctagaa tgtttgactc    5160
agcaaattca caggctcatc tttctaactt gatggtgaat atggaaattc agctaaatgg    5220
```

-continued

| | |
|---|---|
| atgttaataa aattcaaacg ttttaaggac agatgaaaat gacagaattt taaggtaaaa | 5280 |
| tatatgaagg aatataagat aaaggatttt tctaccttca gcaaaaacat acccactaat | 5340 |
| tagtaaaatt aataggcaaa aaaaagttgc atgctcttat actgtaatga ttatcatttt | 5400 |
| aaaactagct ttttgccttc gagctatcgg ggtaaagacc tacaggaaaa ctactgtcga | 5460 |
| aatcctcgag gggaagaagg gggaccctgg tgtttcacaa gcaatccaga ggtacgctac | 5520 |
| gaagtctgtg acattcctca gtgttcagaa gttgaatgca tgacctgcaa tggggagagt | 5580 |
| tatcgaggtc tcatggatca tacagaatca ggcaagattt gtcagcgctg ggatcatcag | 5640 |
| acaccacacc ggcacaaatt cttgcctgaa agatatcccg acaagggctt tgatgataat | 5700 |
| tattgccgca atcccgatgg ccagccgagg ccatggtgct atactcttga ccctcacacc | 5760 |
| cgctgggagt actgtgcaat taaaacatgc gctgacaata ctatgaatga cactgatgtt | 5820 |
| cctttggaaa caactgaatg catccaaggt caaggagaag gctacagggg cactgtcaat | 5880 |
| accatttgga tggaattcc atgtcagcgt tgggattctc agtatcctca cgagcatgac | 5940 |
| atgactcctg aaaatttcaa gtgcaaggac ctacgagaaa attactgccg aaatccagat | 6000 |
| gggtctgaat caccctggtg ttttaccact gatccaaaca tccgagttgg ctactgctcc | 6060 |
| caaattccaa actgtgatat gtcacatgga caagattgtt atcgtgggaa tggcaaaaat | 6120 |
| tatatgggca acttatccca aacaagatct ggactaacat gttcaatgtg ggacaagaac | 6180 |
| atggaagact acatcgtca tatcttctgg gaaccagatg caagtaagct gaatgagaat | 6240 |
| tactgccgaa atccagatga tgatgctcat ggaccctggt gctacacggg aaatccactc | 6300 |
| attccttggg attattgccc tatttctcgt tgtgaaggtg ataccacacc tacaatagtc | 6360 |
| aatttagacc atcccgtaat atcttgtgcc aaaacgaaac aattgcgagt tgtaaatggg | 6420 |
| attccaacac gaacaaacat aggatggatg gttagtttga gatacagaaa taacatatc | 6480 |
| tgcggaggat cattgataaa ggagagttgg gttcttactg cacgacagtg tttcccttct | 6540 |
| cgagacttga agattatga agcttggctt ggaattcatg atgtccacgg aagaggagat | 6600 |
| gagaaatgca acaggttct caatgtttcc cagctggtat atggccctga aggatcagat | 6660 |
| ctggttttaa tgaagcttgc caggcctgct gtcctggatg attttgttag tacgattgat | 6720 |
| ttacctaatt atggatgcac aattcctgaa aagaccagtt gcagtgttta tggctggggc | 6780 |
| tacactggat tgatcaacta tgatggccta ttacgagtgg cacatctcta tataatggga | 6840 |
| aatgagaaat gcagccagca tcatcgaggg aaggtgactc tgaatgagtc tgaaatatgt | 6900 |
| gctggggctg aaaagattgg atcaggacca tgtgaggggg attatggtgg cccacttgtt | 6960 |
| tgtgagcaac ataaaatgag aatggttctt ggtgtcattg ttcctggtcg tggatgtgcc | 7020 |
| attccaaatc gtcctggtat ttttgtccga gtagcatatt atgcaaaatg gatacacaaa | 7080 |
| attattttaa catataaggt accacagtca tag | 7113 |

<210> SEQ ID NO 3
<211> LENGTH: 34
<212> TYPE: DNA
<213> ORGANISM: Artificial Sequence
<220> FEATURE:
<223> OTHER INFORMATION: gHGF3 primer

<400> SEQUENCE: 3
gtaaaggacg cgtctacaag ggaacagtat ctat          34

```
<210> SEQ ID NO 4
<211> LENGTH: 27
<212> TYPE: DNA
<213> ORGANISM: Artificial Sequence
<220> FEATURE:
<223> OTHER INFORMATION: gHGF4 primer

<400> SEQUENCE: 4
actggatcct ctcggccata aacatct                                            27

<210> SEQ ID NO 5
<211> LENGTH: 34
<212> TYPE: DNA
<213> ORGANISM: Artificial Sequence
<220> FEATURE:
<223> OTHER INFORMATION: gHGF10 primer

<400> SEQUENCE: 5
gaagcttagc accatgtggg tgaccaaact cctg                                    34

<210> SEQ ID NO 6
<211> LENGTH: 27
<212> TYPE: DNA
<213> ORGANISM: Artificial Sequence
<220> FEATURE:
<223> OTHER INFORMATION: gHGF5 primer

<400> SEQUENCE: 6
tggccgagag gatccagtat attaata                                            27

<210> SEQ ID NO 7
<211> LENGTH: 27
<212> TYPE: DNA
<213> ORGANISM: Artificial Sequence
<220> FEATURE:
<223> OTHER INFORMATION: gHGF7 primer

<400> SEQUENCE: 7
cccctcgagg atttcgacag tagtttt                                            27

<210> SEQ ID NO 8
<211> LENGTH: 28
<212> TYPE: DNA
<213> ORGANISM: Artificial Sequence
<220> FEATURE:
<223> OTHER INFORMATION: gHGF12 primer

<400> SEQUENCE: 8
gggatccctt cctttctacc tgtatttg                                           28

<210> SEQ ID NO 9
<211> LENGTH: 25
<212> TYPE: DNA
<213> ORGANISM: Artificial Sequence
<220> FEATURE:
<223> OTHER INFORMATION: gHGF13 primer

<400> SEQUENCE: 9
gggatcctgg gtaaacacat ttgaa                                              25

<210> SEQ ID NO 10
<211> LENGTH: 28
<212> TYPE: DNA
<213> ORGANISM: Artificial Sequence
<220> FEATURE:
<223> OTHER INFORMATION: gHGF6 primer
```

<400> SEQUENCE: 10
gggatcctta tgtttcagac aacttcga                28

<210> SEQ ID NO 11
<211> LENGTH: 34
<212> TYPE: DNA
<213> ORGANISM: Artificial Sequence
<220> FEATURE:
<223> OTHER INFORMATION: gHGF1 primer

<400> SEQUENCE: 11
gaagcttgcc accatgtggg tgaccaaact cctg          34

<210> SEQ ID NO 12
<211> LENGTH: 34
<212> TYPE: DNA
<213> ORGANISM: Artificial Sequence
<220> FEATURE:
<223> OTHER INFORMATION: gHGF2 primer

<400> SEQUENCE: 12
gggatccaga acgcgtcctt taccgatgat gcag          34

<210> SEQ ID NO 13
<211> LENGTH: 35
<212> TYPE: DNA
<213> ORGANISM: Artificial Sequence
<220> FEATURE:
<223> OTHER INFORMATION: gHGF8 primer

<400> SEQUENCE: 13
gggatccctt ctcgagactt gaaagattat gaagc         35

<210> SEQ ID NO 14
<211> LENGTH: 32
<212> TYPE: DNA
<213> ORGANISM: Artificial Sequence
<220> FEATURE:
<223> OTHER INFORMATION: gHGF9 primer

<400> SEQUENCE: 14
gtctagagcg gccgctatga ctgtggtacc tt            32

<210> SEQ ID NO 15
<211> LENGTH: 36
<212> TYPE: DNA
<213> ORGANISM: Artificial Sequence
<220> FEATURE:
<223> OTHER INFORMATION: cHGF5 primer

<400> SEQUENCE: 15
ggatccacgc gtagcagcac catgtgggtg accaaa        36

<210> SEQ ID NO 16
<211> LENGTH: 36
<212> TYPE: DNA
<213> ORGANISM: Artificial Sequence
<220> FEATURE:
<223> OTHER INFORMATION: cHGF3 primer

<400> SEQUENCE: 16
ggatcctcta gattacttca gctatgactg tggtac        36

```
<210> SEQ ID NO 17
<211> LENGTH: 26
<212> TYPE: DNA
<213> ORGANISM: Artificial Sequence
<220> FEATURE:
<223> OTHER INFORMATION: GHGF5' primer

<400> SEQUENCE: 17
caaatgtcag ccctggagtt ccatga                                         26

<210> SEQ ID NO 18
<211> LENGTH: 23
<212> TYPE: DNA
<213> ORGANISM: Artificial Sequence
<220> FEATURE:
<223> OTHER INFORMATION: GHGF3' primer

<400> SEQUENCE: 18
ctggattgct tgtgaaacag ggt                                            23

<210> SEQ ID NO 19
<211> LENGTH: 4679
<212> TYPE: DNA
<213> ORGANISM: Artificial Sequence
<220> FEATURE:
<223> OTHER INFORMATION: HGF-X6 gene

<400> SEQUENCE: 19
atgtgggtga ccaaactcct gccagccctg ctgctgcagc atgtcctcct gcatctcctc    60
ctgctcccca tcgccatccc ctatgcagag ggacaaagga aagaagaaa tacaattcat    120 gaattcaaaa atcagcaaa gactacccta atcaaaatag atccagcact gaagataaaa    180
accaaaaaag tgaatactgc agaccaatgt gctaatagat gtactaggaa taaggactt    240 ccattcactt gcaaggcttt tgttttttgat aaagcaagaa acaatgcct ctggttcccc    300 ttcaatagca tgtcaagtgg agtgaaaaaa gaatttggcc atgaatttga cctctatgaa    360 acaaagact acattagaaa ctgcatcatc ggtaaaggac gcagctacaa gggaacagta    420
tctatcacta gagtggcat caaatgtcag ccctggagtt ccatgataccacacgaaacac    480 aggtaagaac agtatgaaga aaagagatga agcctctgtc tttttttacat gttaacagtc    540 tcatattagt ccttcagaat aattctacaa tcctaaaata acttagccaa cttgctgaat    600
tgtattacgg caaggtttat atgaattcat gactgatatt tagcaaatga ttaattaata    660
tgttaataaa atgtagccaa acaatatct taccttaatg cctcaatttg tagatctcgg    720
tatttgtgga tcccttcctt tctacctgta tttgtcctaa taaattgttg acttattaat    780
tcactacttc ctcacagctt ttttttggct ttacaaatcc actggaaagg tatatggtg     840 tatcactttg tgtatttcgg tgtgcatgtg tagagggac aaaaatcctc tctcaaacta    900
taaatattga gtatttgtgt attgaacatt tgctataact actaggtttc ttaaataatc    960
ttaatatata aaatgatata gaaaaaggga aattatagtt cgtattattc atctaagtga   1020
agagattaaa acccagggag taaataaatt gtctaaggac taaggttgta tactatttag   1080
gtgatagata tggggcaacc gtatgggttt tatgattaac aaataacctt ctcaccactc   1140
taccatatca acttttccat aaaagagagc tatagtattc tttgcttaaa taaatttgat   1200
tagtgcatga cttcttgaaa acatataaag caaaagtcac atttgattct atcagaaaag   1260
tgagtaagcc atggcccaaa caaagatgc attaaaatat tctggaatga tggagctaaa   1320
agtaagaaaa atgactttt aaaaaagttt actgttagga attgtgaaat tatgctgaat   1380
tttagttgca ttataatttt tgtcagtcat acggtctgac aacctgtctt atttctattt   1440
```

```
ccccatatga ggaatgctag ttaagtatgg atattaacta ttactactta gatgcattga    1500
agttgcataa tatggataat acttcactgg ttccctgaaa atgtttagtt agtaataagt    1560
ctcttacact atttgttttg tccaataatt tatattttct gaagacttaa ctctagaata    1620
cactcatgtc aaaatgaaag aatttcattg caaatattg cttggtacat gacgcatacc     1680
tgtatttgtt ttgtgtcaca acatgaaaaa tgatggttta ttagaagttt cattgggtag    1740
gaaacacatt tgaatggtat ttactaagat actaaaatcc ttggacttca ctctaatttt    1800
agtgccattt agaactcaag gtctcagtaa aagtagaaat aaagcctgtt aacaaaacac    1860
aagctgaata ttaaaaatgt aactggattt tcaaagaaat gtttactggt attacctgta    1920
gatgtatatt ctttattatg atcttttgtg taaagtctgg cagacaaatg caatatctaa    1980
ttgttgagtc caatatcaca agcagtacaa agtataaaa aagacttggc cttttctaat     2040
gtgttaaaat actttatgct ggtaataaca ctaagagtag ggcactagaa attttaagtg    2100
aagataatgt gttgcagtta ctgcactcaa tggcttacta ttataaacca aaactgggat    2160
cactaagctc cagtcagtca aaatgatcaa aattattgaa gagaataagc aattctgttc    2220
tttattagga cacagtagat acagactaca agtggagtg tgcttaataa gaggtagcat     2280
ttgttaagtg tcaattactc tattatccct tggagcttct caaaataacc atataaggtg    2340
taagatgtta aaggttatgg ttacactcag tgcacaggta agctaatagg ctgagagaag    2400
ctaaattact tactggggtc tcacagtaag aaagtgagct gaagtttcag cccagattta    2460
actggattct gggctcttta ttcatgttac ttcatgaatc tgtttctcaa ttgtgcagaa    2520 aaaggggc tatttataag aaaagcaata aacaaacaag taatgatctc aaataagtaa      2580
tgcaagaaat agtgagattt caaaatcagt ggcagcgatt tctcagttct gtcctaagtg    2640
gccttgctca atcacctgct atcttttagt ggagctttga aattatgttt cagacaactt    2700
cgattcagtt ctagaatgtt tgactcagca aattcacagg ctcatctttc taacttgatg    2760
gtgaatatgg aaattcagct aaatggatgt taataaaatt caaacgtttt aaggacagat    2820
gaaaatgaca gaattttaag gtaaaatata tgaaggaata taagataaag gattttcta    2880 ccttcagcaa aaacataccc actaattagt aaaattaata ggcaaaaaaa agttgcatgc    2940
tcttatactg taatgattat cattttaaaa ctagcttttt gccttcgagc tatcggggta    3000
aagacctaca ggaaaactac tgtcgaaatc ctcgaggga agaaggggga ccctggtgtt     3060
tcacaagcaa tccagaggta cgctacgaag tctgtgacat tcctcagtgt tcagaagttg    3120
aatgcatgac ctgcaatggg gagagttatc gaggtctcat ggatcataca gaatcaggca    3180
agatttgtca gcgctgggat catcagacac cacaccggca caaattcttg cctgaaagat    3240
atcccgacaa gggctttgat gataattatt gccgcaatcc cgatggccag ccgaggccat    3300
ggtgctatac tcttgaccct cacacccgct gggagtactg tgcaattaaa acatgcgctg    3360
acaatactat gaatgacact gatgttcctt tggaaacaac tgaatgcatc caaggtcaag    3420
gagaaggcta caggggcact gtcaatacca tttggaatgg aattccatgt cagcgttggg    3480
attctcagta tcctcacgag catgacatga ctcctgaaaa tttcaagtgc aaggacctac    3540
gagaaaatta ctgccgaaat ccagatgggt ctgaatcacc ctggtgtttt accactgatc    3600
caaacatccg agttggctac tgctcccaaa ttccaaactg tgatatgtca catggacaag    3660
attgttatcg tgggaatggc aaaaattata tgggcaactt atcccaaaca agatctggac    3720
taacatgttc aatgtgggac aagaacatgg aagacttaca tcgtcatatc ttctgggaac    3780
cagatgcaag taagctgaat gagaattact gccgaaatcc agatgatgat gctcatggac    3840
```

```
cctggtgcta cacgggaaat ccactcattc cttgggatta ttgccctatt tctcgttgtg    3900
aaggtgatac cacacctaca atagtcaatt tagaccatcc cgtaatatct tgtgccaaaa    3960
cgaaacaatt gcgagttgta aatgggattc caacacgaac aaacatagga tggatggtta    4020
gtttgagata cagaaataaa catatctgcg gaggatcatt gataaaggag agttgggttc    4080
ttactgcacg acagtgtttc ccttctcgag acttgaaaga ttatgaagct tggcttggaa    4140
ttcatgatgt ccacggaaga ggagatgaga atgcaaaca ggttctcaat gtttcccagc     4200
tggtatatgg ccctgaagga tcagatctgg ttttaatgaa gcttgccagg cctgctgtcc    4260
tggatgattt tgttagtacg attgatttac ctaattatgg atgcacaatt cctgaaaaga    4320
ccagttgcag tgtttatggc tggggctaca ctggattgat caactatgat ggcctattac    4380
gagtggcaca tctctatata atgggaaatg agaaatgcag ccagcatcat cgagggaagg    4440
tgactctgaa tgagtctgaa atatgtgctg gggctgaaaa gattggatca ggaccatgtg    4500 aggggggatta tggtggccca cttgtttgtg agcaacataa aatgagaatg gttcttggtg    4560
tcattgttcc tggtcgtgga tgtgccattc caaatcgtcc tggtattttt gtccgagtag    4620
catattatgc aaaatggata cacaaaatta ttttaacata aaggtaccca cagtcatag    4679

<210> SEQ ID NO 20
<211> LENGTH: 3679
<212> TYPE: DNA
<213> ORGANISM: Artificial Sequence
<220> FEATURE:
<223> OTHER INFORMATION: HGF-X7 gene

<400> SEQUENCE: 20
atgtgggtga ccaaactcct gccagccctg ctgctgcagc atgtcctcct gcatctcctc      60
ctgctcccca tcgccatccc ctatgcagag ggacaaagga aaagaagaaa tacaattcat     120
gaattcaaaa aatcagcaaa gactacccta atcaaaatag atccagcact gaagataaaa     180
accaaaaaag tgaatactgc agaccaatgt gctaatagag tactaggaa taaaggactt      240 ccattcactt gcaaggcttt tgttttttgat aaagcaagaa acaatgcct ctggttcccc      300 ttcaatagca tgtcaagtgg agtgaaaaaa gaatttggcc atgaatttga cctctatgaa     360
aacaaagact acattagaaa ctgcatcatc ggtaaaggac gcagctacaa gggaacagta     420
tctatcacta gagtggcat caaatgtcag ccctggagtt ccatgatacc acacgaacac      480
aggtaagaac agtatgaaga aaagagatga agcctctgtc ttttttacat gttaacagtc      540
tcatatatgt ccttcagaat aattctacaa tcctaaaata acttagccaa cttgctgaat     600
tgtattacgg caaggtttat atgaattcat gactgatatt tagcaaatga ttaattaata     660
tgttaataaa atgtagccaa aacaatatct taccttaatg cctcaatttg tagatctcgg    720
tatttgtgga tcctgggtag gaaacacatt tgaatggtat ttactaagat actaaaatcc    780
ttggacttca ctctaatttt agtgccattt agaactcaag gtctcagtaa agtagaaat      840 aaagcctgtt aacaaaacac aagctgaata ttaaaaatgt aactggatt tcaaagaaat     900 gtttactggt attacctgta gatgtatatt cttattatg atcttttgtg taaagtctgg      960
cagacaaatg caatatctaa ttgttgagtc caatatcaca agcagtacaa agtataaaa     1020 aagacttggc cttttctaat gtgttaaaat actttatgct ggtaataaca ctaagagtag    1080
ggcactagaa attttaagtg aagataatgt gttgcagtta ctgcactcaa tggcttacta    1140
ttataaacca aaactgggat cactaagctc cagtcagtca aaatgatcaa aattattgaa    1200
gagaataagc aattctgttc tttattagga cacagtagat acagactaca aagtggagtg    1260
```

```
tgcttaataa gaggtagcat tgttaagtg tcaattactc tattatccct tggagcttct      1320
caaaataacc atataaggtg taagatgtta aaggttatgg ttacactcag tgcacaggta      1380
agctaatagg ctgagagaag ctaaattact tactggggtc tcacagtaag aaagtgagct      1440
gaagtttcag cccagattta actgattct gggctcttta ttcatgttac ttcatgaatc       1500
tgtttctcaa ttgtgcagaa aaagggggc tatttataag aaaagcaata acaaacaag        1560
taatgatctc aaataagtaa tgcaagaaat agtgagattt caaaatcagt ggcagcgatt      1620
tctcagttct gtcctaagtg gccttgctca atcacctgct atcttttagt ggagctttga      1680
aattatgttt cagacaactt cgattcagtt ctagaatgtt tgactcagca aattcacagg      1740
ctcatctttc taacttgatg gtgaatatgg aaattcagct aaatggatgt taataaaatt      1800
caaacgtttt aaggacagat gaaaatgaca gaattttaag gtaaaatata tgaaggaata     1860
taagataaag gatttttcta ccttcagcaa aaacataccc actaattagt aaaattaata     1920
ggcaaaaaaa agttgcatgc tcttatactg taatgattat cattttaaaa ctagcttttt     1980
gccttcgagc tatcgggta aagacctaca ggaaaactac tgtcgaaatc ctcgaggga       2040
agaaggggga ccctggtgtt tcacaagcaa tccagaggta cgctacgaag tctgtgacat     2100
tcctcagtgt tcagaagttg aatgcatgac ctgcaatggg gagagttatc gaggtctcat     2160
ggatcataca gaatcaggca agatttgtca gcgctgggat catcagacac cacaccggca     2220
caaattcttg cctgaaagat atcccgacaa gggctttgat gataattatt gccgcaatcc     2280
cgatggccag ccgaggccat ggtgctatac tcttgacct cacacccgct gggagtactg      2340
tgcaattaaa acatgcgctg acaatactat gaatgacact gatgttcctt tggaaacaac     2400
tgaatgcatc caaggtcaag gagaaggcta caggggcact gtcaatacca tttggaatgg     2460
aattccatgt cagcgttggg attctcagta tcctcacgag catgacatga ctcctgaaaa     2520
tttcaagtgc aaggacctac gagaaaatta ctgccgaaat ccagatgggc tgaatcacc     2580
ctggtgtttt accactgatc caaacatccg agttggctac tgctcccaaa ttccaaactg     2640
tgatatgtca catggacaag attgttatcg tgggaatggc aaaaattata tgggcaactt     2700
atcccaaaca gatctggac taacatgttc aatgtgggac aagaacatgg aagacttaca     2760
tcgtcatatc ttctgggaac cagatgcaag taagctgaat gagaattact gccgaaatcc     2820
agatgatgat gctcatggac cctggtgcta cacgggaaat ccactcattc cttgggatta     2880
ttgcccctatt tctcgttgtg aaggtgatac cacacctaca atagtcaatt tagaccatcc     2940
cgtaatatct tgtgccaaaa cgaaacaatt gcgagttgta atgggattc caacacgaac      3000
aaacatagga tggatggtta gtttgagata cagaaataaa catatctgcg gaggatcatt     3060
gataaaggag agttgggttc ttactgcacg acagtgtttc ccttctcgag acttgaaaga     3120
ttatgaagct tggcttggaa ttcatgatgt ccacggaaga ggagatgaga atgcaaaca     3180
ggttctcaat gtttcccagc tggtatatgg ccctgaagga tcagatctgg tttaatgaa      3240
gcttgccagg cctgctgtcc tggatgattt tgttagtacg attgatttac ctaattatgg     3300
atgcacaatt cctgaaaaga ccagttgcag tgtttatggc tggggctaca ctggattgat     3360
caactatgat ggcctattac gagtggcaca tctctatata tgggaaatg agaaatgcag      3420
ccagcatcat cgagggaagg tgactctgaa tgagtctgaa atatgtgctg ggctgaaaa      3480
gattggatca ggaccatgtg aggggattga tggtggccca cttgtttgtg agcaacataa     3540
aatgagaatg gttcttggtg tcattgttcc tggtcgtgga tgtgccattc caaatcgtcc     3600
```

-continued

<210> SEQ ID NO 21
<211> LENGTH: 2729
<212> TYPE: DNA
<213> ORGANISM: Artificial Sequence
<220> FEATURE:
<223> OTHER INFORMATION: HGF-X8 gene

<400> SEQUENCE: 21

```
atgtgggtga ccaaactcct gccagccctg ctgctgcagc atgtcctcct gcatctcctc      60
ctgctcccca tcgccatccc ctatgcagag ggacaaagga aagaagaaa tacaattcat     120
gaattcaaaa atcagcaaa gactaccct atcaaaatag atccagcact gaagataaaa     180
accaaaaaag tgaatactgc agaccaatgt gctaatagat gtactaggaa taaggactt     240
ccattcactt gcaaggcttt tgtttttgat aaagcaagaa acaatgcct ctggttcccc     300
ttcaatagca tgtcaagtgg agtgaaaaaa gaatttggcc atgaatttga cctctatgaa     360
aacaaagact acattagaaa ctgcatcatc ggtaaaggac gcagctacaa gggaacagta     420
tctatcacta gagtggcat caaatgtcag ccctggagtt ccatgatacc acacgaacac     480
aggtaagaac agtatgaaga aaagagatga agcctctgtc ttttttacat gttaacagtc     540
tcatattagt ccttcagaat aattctacaa tcctaaaata acttagccaa cttgctgaat     600
tgtattacgg caaggtttat atgaattcat gactgatatt tagcaaatga ttaattaata     660
tgttaataaa atgtagccaa acaatatct taccttaatg cctcaatttg tagatctcgg     720
tatttgtgga tccttatgtt tcagacaact tcgattcagt tctagaatgt ttgactcagc     780
aaattcacag gctcatcttt ctaacttgat ggtgaatatg gaaattcagc taaatggatg     840
ttaataaaat tcaaacgttt taaggacaga tgaaaatgac agaatttaa ggtaaaatat     900
atgaaggaat ataagataaa ggattttct accttcagca aaaacatacc cactaattag     960
taaaattaat aggcaaaaaa aagttgcatg ctcttatact gtaatgatta tcattttaaa    1020
actagctttt tgccttcgag ctatcggggt aaagacctac aggaaaacta ctgtcgaaat    1080
cctcgagggg aagaagggg accctggtgt ttcacaagca atccagaggt acgctacgaa    1140
gtctgtgaca ttcctcagtg ttcagaagtt gaatgcatga cctgcaatgg ggagagttat    1200
cgaggtctca tggatcatac agaatcaggc aagatttgtc agcgctggga tcatcagaca    1260
ccacaccggc acaaattctt gcctgaaaga tatcccgaca agggcttga tgataattat    1320
tgccgcaatc ccgatggcca gccgaggcca tggtgctata ctcttgaccc tcacacccgc    1380
tgggagtact gtgcaattaa acatgcgct gacaatacta tgaatgacac tgatgttcct    1440
ttggaaacaa ctgaatgcat ccaaggtcaa ggagaaggct acaggggcac tgtcaatacc    1500
atttggaatg gaattccatg tcagcgttgg gattctcagt atcctcacga gcatgacatg    1560
actcctgaaa atttcaagtg caaggaccta cgagaaaatt actgccgaaa tccagatggt    1620
ctgaatcacc ctggtgtttt accactgatc caaacatccg agttggctac tgctcccaaa    1680
ttccaaactg tgatatgtca catggacaag attgttatcg tgggaatggc aaaaattata    1740
tgggcaactt atccccaaaca agatctggac taacatgttc aatgtgggac aagaacatgg    1800
aagacttaca tcgtcatatc ttctgggaac cagatgcaag taagctgaat gagaattact    1860
gccgaaatcc agatgatgat gctcatggac cctggtgcta cacgggaaat ccactcattc    1920
cttgggatta ttgccctatt tctcgttgtg aaggtgatac cacacctaca atagtcaatt    1980
```

```
tagaccatcc cgtaatatct tgtgccaaaa cgaaacaatt gcgagttgta aatgggattc    2040
caacacgaac aaacatagga tggatggtta gtttgagata cagaaataaa catatctgcg    2100
gaggatcatt gataaaggag agttgggttc ttactgcacg acagtgtttc ccttctcgag    2160
acttgaaaga ttatgaagct tggcttggaa ttcatgatgt ccacggaaga ggagatgaga    2220
aatgcaaaca ggttctcaat gtttcccagc tggtatatgg ccctgaagga tcagatctgg    2280 tttttaatgaa gcttgccagg cctgctgtcc tggatgattt tgttagtacg attgatttac    2340
ctaattatgg atgcacaatt cctgaaaaga ccagttgcag tgtttatggc tggggctaca    2400
ctggattgat caactatgat ggcctattac gagtggcaca tctctatata atgggaaatg    2460
agaaatgcag ccagcatcat cgagggaagg tgactctgaa tgagtctgaa atatgtgctg    2520
gggctgaaaa gattggatca ggaccatgtg aggggatta tggtggccca cttgtttgtg    2580
agcaacataa aatgagaatg gttcttggtg tcattgttcc tggtcgtgga tgtgccattc    2640
caaatcgtcc tggtatttt gtccgagtag catattatgc aaaatggata cacaaaatta    2700
ttttaacata taaggtacca cagtcatag                                     2729
```